US006774223B2

(12) United States Patent
Macina et al.

(10) Patent No.: US 6,774,223 B2
(45) Date of Patent: Aug. 10, 2004

(54) METHOD OF DIAGNOSING, MONITORING, STAGING, IMAGING AND TREATING COLON CANCER

(75) Inventors: Roberto A. Macina, San Jose, CA (US); Rajeswari Pillai, Redwood City, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/895,652

(22) Filed: Jun. 28, 2001

(65) Prior Publication Data

US 2002/0081640 A1 Jun. 27, 2002

Related U.S. Application Data

(60) Provisional application No. 60/214,515, filed on Jun. 28, 2000.

(51) Int. Cl.[7] .............................................. C07K 21/02

(52) U.S. Cl. ..................................... 536/23.1; 536/23.5

(58) Field of Search .............................. 536/23.1, 23.5; 530/350; 424/184.1, 185.1, 277.1

(56) References Cited

U.S. PATENT DOCUMENTS

| | | | | |
|---|---|---|---|---|
| 4,544,545 | A | 10/1985 | Ryan et al. | 424/1.1 |
| 4,873,191 | A | 10/1989 | Wagner et al. | 435/172.3 |
| 4,946,778 | A | 8/1990 | Ladner et al. | 435/69.6 |
| 5,580,859 | A | 12/1996 | Felgner et al. | 514/44 |
| 5,693,622 | A | 12/1997 | Wolff et al. | 514/44 |
| 5,705,151 | A | 1/1998 | Dow et al. | 424/93.21 |
| 6,468,758 | B1 | 10/2002 | Benson et al. | 435/7.23 |

FOREIGN PATENT DOCUMENTS

| | | | |
|---|---|---|---|
| EP | 0 394 827 | | 4/1990 |
| EP | 1 074 617 | A2 | 2/2001 |
| JP | WO 02/053737 | A1 | 7/2002 |
| WO | WO 90/11092 | | 10/1990 |
| WO | WO 96/34891 | | 11/1996 |
| WO | WO 98/11779 | | 3/1998 |
| WO | WO 01/54733 | A1 | 8/2001 |
| WO | WO 01/55163 | A1 | 8/2001 |
| WO | 70807 | * | 9/2001 |
| WO | WO 01/79556 | A2 | 10/2001 |
| WO | WO 02/30963 | A1 | 4/2002 |
| WO | WO 02/031111 | A3 | 4/2002 |

OTHER PUBLICATIONS

Spitler et al, Cancer Biotherapy vol. 10 p. 1 (1995).*
Ezzell, J. NIH Research, vol. 7 p. 46 (1995).*
Skolnick et al, TIBTECH vol. 18, p. 34 (2000).*
Abdullah et al., "Non–viral gene transfer:Applications in developmental biology and gene therapy", *Biol. Cell* 1995 85(1):1–7.
Beal and Dervan, "Second Structural Motif for Recognition of DNA by Oligonucleotide–Directed Triple–Helix Formation", 191 *Science* 251:1360–1363.
Chao et al., "Experimental kallikrein Gene Therapy in Hypertension, Cardiovascular and Renall Diseases", *Pharmacol. Res.* 1997 35(6):517–522.
Cole et al., "The EBV Hybridoma Technique and Its Application to Human Lung Cancer", 77–96 *Monoclonal Antibodies and Cancer Therapy, Alan R. Liss, Inc.*
Coligan et al., *Current Protocols in Immunology 1(2): Chapter 5* 1991.
Cooney et al., "Site–Specific Oligonucleotide Binding Represses Transcription of the Human c–myc Gene in Vitro", 1988 *Science* 241:456–459.
Gluzman Y., "SV40–Transformed Simian Cells Support the Replication of Early SV40 Mutants", *Cell* 1981 23:175–182.
Griffin et al., "Initial Clinical Study of Indium–111–Labeled Clone 110 Anticarcinoembryonic Antigen Antibody in Patients With Colorectal Cancer", 1991 *J. Clin. Onc.* 9:631–640.
Felgner et al., "Improved Cationic Lipid Formulations for In Vivo Gene Therapy", *Ann. NY Acad. Sci.* 1995 722:126–139.
Köhler G. and Milstein C., "Continuous cultures of fused cells secreting antibody of predefined specificity", 1975 *Nature* 256:495–497.
Kozbor et al., "The production of monoclonal antibodies from human lymphocytes", 1983 *Immunology Today* 4:72–78.
Kirschmeier et al., "Construction and Characterization of a Retroviral Vector demonstrating Efficient Expression of cloned cDNA Sequences", *DNA* 1988 7(3):219–225.
Lauffer R.B., "Targeted Relaxation Enhancement Agents for MRI", 1991 *Magnetic Resonance in Medicine* 22:339–342.
Lee et al., "Complexes formed by (pyrimidine)$_n$ (purine)$_n$ DNAs on lowering the pH are three–stranded", 1979 *Nucleic Acids Research* 6:3073–3091.
Rattan et al., Protein Synthesis: Posttranslational Modifications and Aging, Ann. N.Y. Acad. Sci. 663:48–62 1992.
Sambrook et al., Molecular Cloning, A Laboratory Manual, 2nd Ed.; Cold Spring Harbor Laboratory Press, Cold Spring Harbor, N.Y. 1989.
Sumerdon et al., "An Optimized Antibody–Chelator Conjugate for Imaging of Carcinoembryonic Antigen with Indium–111", 1990 *Nucl. Med. Biol.* 17:247–254.
Wold, F., Posttranslational Protein Modifications: Perspectives and Prospects Posttranslational Covalent Modification of Proteins, B. C. Johnson, Ed., Academic Press, New York 1983.

(List continued on next page.)

*Primary Examiner*—Sheela Huff
(74) *Attorney, Agent, or Firm*—Licata & Tyrrell P.C.; Nathan P. Letts

(57) ABSTRACT

The invention relates to CSG polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

1 Claim, No Drawings

OTHER PUBLICATIONS

Proteins Structure and Molecular Properties, 2nd Ed., T. E. Creighton, W. H. Freeman and Company, New York 1993.

Okano et al., "Myelin Basic Protein Gene and the Function of Antisense RNA in Its Repression in Myelin–Deficient Mutant Mouse", *J. Neurochem.* 1991 56:560.

Tabata et al., Arterial gene transfer of acidic fibroblast growth factor for therapeutic angiogenesis in vivo:critical role of secretion signal in use of naked DNA, *Cardiovasc. Res.* 1997 35(3):470–479.

Tsurumi et al., "Direct Intramuscular Gene Transfer of Naked DNA Encoding Vascular Endothelial Growth Factor Augments Collateral Development and Tissue Perfusion", *Circulation* 1994 94(12):3271–3290.

Verma et al., Human Chromosomes:A Manual of Basic Techniques, Pergamon Press, New York 1988.

Kimura et al., "Accumulation of GTP–bound RhoA during cytokinesis and a critical role of ECT2 in this accumulation", J. Biol. Chem. 2000 275:17233–17236.

Miki et al., "Oncogene ect2 is related to regulators of small GTP–binding proteins", Nature 1993 326:462–465.

Takai et al., "Chromosomal localization of the human ECT2 Protooncogene to 3q26.1–q26.2 by Somatic Cell Analysis and Fluorescence in *Situ* Hybridization", Genomics 1995 27:220–222.

Tatsumoto et al., "Human ECT2 is an exchange factor for Rho GTPases, phosphorylated in G2/M phases, and involved in cytokinesis", J. Cell Biol. 1999 147:921–927.

GenBank Database GI No. 21735571, Accession No. NM_018098 "Homo sapiens epithelial cell transforming sequence 2 oncogene (ECT2), mRNA", PRI Dec. 21, 2003.

GenBank Database GI No. 34978931, Accession No. AY376439 "Homo sapiens epithelial cell transforming 2 (ECT2) mRNA, complete cds.", PRI Sep. 29, 2003.

GenBank Database GI No. 14042598, Accession No. AK027713 "Homo sapiens cDNA FLJ14807 fis, clone NT2RP4001760, weakly similar to Putative RHO/RAC Guanine Nucleotide Exchange Factor", PRI Aug. 1, 2002.

GenBank Database GI No. 7022507, Accession No. AK001323 "Homo sapiens cDNA FLJ10461 fis, clone NT2RP1001482", PRI Aug. 1, 2002.

GenBank Database GI No. 13905103, Accession No. BC006838 "Homo sapiens epithelial cell transforming sequence 2 oncogene, mRNA (cDNA clone IMAGE:3450287), complete CDs.", PRI Sep. 16, 2003.

GenBank Database GI No. 10435125, Accession No. AK023267 "Homo sapiens cDNA FLJ13205 fis, clone NTRP3004534, highly similar to Mouse oncogne (ect2) mRNA", PRI Aug. 1, 2002.

* cited by examiner

METHOD OF DIAGNOSING, MONITORING, STAGING, IMAGING AND TREATING COLON CANCER

INTRODUCTION

This application claims the benefit of priority from U.S. provisional application Ser. No. 60/214,515 filed Jun. 28, 2000.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists for detecting, diagnosing, monitoring, staging, prognosticating, imaging and treating cancers, particularly colon cancer. In particular, in these and in other regards, the invention relates to colon specific polynucleotides and polypeptides hereinafter referred to as colon specific genes or "CSGs".

BACKGROUND OF THE INVENTION

Cancer of the colon is a highly treatable and often curable disease when localized to the bowel. It is one of the most frequently diagnosed malignancies in the United States as well as the second most common cause of cancer death. Surgery is the primary treatment and results in cure in approximately 50% of patients. However, recurrence following surgery is a major problem and often is the ultimate cause of death.

The prognosis of colon cancer is clearly related to the degree of penetration of the tumor through the bowel wall and the presence or absence of nodal involvement. These two characteristics form the basis for all staging systems developed for this disease. Treatment decisions are usually made in reference to the older Duke's or the Modified Astler-Coller (MAC) classification scheme for staging.

Bowel obstruction and bowel perforation are indicators of poor prognosis in patients with colon cancer. Elevated pretreatment serum levels of carcinoembryonic antigen (CEA) and of carbohydrate antigen 19-9 (CA 19-9) also have a negative prognostic significance.

Age greater than 70 years at presentation is not a contraindication to standard therapies. Acceptable morbidity and mortality, as well as long-term survival, are achieved in this patient population.

Because of the frequency of the disease (approximately 160,000 new cases of colon and rectal cancer per year), the identification of high-risk groups, the demonstrated slow growth of primary lesions, the better survival of early-stage lesions, and the relative simplicity and accuracy of screening tests, screening for colon cancer should be a part of routine care for all adults starting at age 50, especially those with first-degree relatives with colorectal cancer.

Procedures used for detecting, diagnosing, monitoring, staging, and prognosticating colon cancer are of critical importance to the outcome of the patient. For example, patients diagnosed with early colon cancer generally have a much greater five-year survival rate as compared to the survival rate for patients diagnosed with distant metastasized colon cancer. New diagnostic methods which are more sensitive and specific for detecting early colon cancer are clearly needed.

Colon cancer patients are closely monitored following initial therapy and during adjuvant therapy to determine response to therapy and to detect persistent or recurrent disease of metastasis. There is clearly a need for a colon cancer marker which is more sensitive and specific in detecting colon cancer, its recurrence, and progression.

Another important step in managing colon cancer is to determine the stage of the patient's disease. Stage determination has potential prognostic value and provides criteria for designing optimal therapy. Generally, pathological staging of colon cancer is preferable over clinical staging because the former gives a more accurate prognosis. However, clinical staging would be preferred were it at least as accurate as pathological staging because it does not depend on an invasive procedure to obtain tissue for pathological evaluation. Staging of colon cancer would be improved by detecting new markers in cells, tissues, or bodily fluids which could differentiate between different stages of invasion.

Accordingly, there is a great need for more sensitive and accurate methods for the staging of colon cancer in a human to determine whether or not such cancer has metastasized and for monitoring the progress of colon cancer in a human which has not metastasized for the onset of metastasis.

In the present invention, methods are provided for detecting, diagnosing, monitoring, staging, prognosticating, imaging and treating colon cancer via colon specific genes referred to herein as CSGs. For purposes of the present invention, CSG refers, among other things, to native protein expressed by the gene comprising a polynucleotide sequence of SEQ ID NO:1, 2, 3, 4, 5, 6, 7, 8, 9, 10, 11, 12, 13, 14, 15, 16, 17, 18 or 19. By "CSG" it is also meant herein polynucleotides which, due to degeneracy in genetic coding, comprise variations in nucleotide sequence as compared to SEQ ID NO: 1, 2, 3, 4, 5, 6, 7, 8, 9, 10, 11, 12, 13, 14, 15, 16, 17, 18 or 19 but which still encode the same protein. In the alternative, what is meant by CSG as used herein, means the native mRNA encoded by the gene comprising the polynucleotide sequence of SEQ ID NO: 1, 2, 3, 4, 5, 6, 7, 8, 9, 10, 11, 12, 13, 14, 15, 16, 17, 18 or 19, levels of the gene comprising the polynucleotide sequence of SEQ ID NO: 1, 2, 3, 4, 5, 6, 7, 8, 9, 10, 11, 12, 13, 14, 15, 16, 17, 18 or 19, or levels of a polynucleotide which is capable of hybridizing under stringent conditions to the antisense sequence of SEQ ID NO: 1, 2, 3, 4, 5, 6, 7, 8, 9, 10, 11, 12, 13, 14, 15, 16, 17, 18 or 19.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide CSGs comprising a polynucleotide of SEQ ID NO: 1, 2, 3, 4, 5, 6, 7, 8, 9, 10, 11, 12, 13, 14, 15, 16, 17, 18, or 19, a protein expressed by a polynucleotide of SEQ ID NO: 1, 2, 3, 4, 5, 6, 7, 8, 9, 10, 11, 12, 13, 14, 15, 16, 17, 18, or 19, or a variant thereof which expresses the protein; or a polynucleotide which is capable of hybridizing under stringent conditions to the antisense sequence of SEQ ID NO:1, 2, 3, 4, 5, 6, 7, 8, 9, 10, 11, 12, 13, 14, 15, 16, 17, 18 or 19.

It is another object of the present invention to provide a method for diagnosing the presence of colon cancer by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with colon cancer.

Further provided is a method of diagnosing metastatic colon cancer in a patient having colon cancer which is not known to have metastasized by identifying a human patient suspected of having colon cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with colon cancer which has metastasized.

Also provided by the invention is a method of staging colon cancer in a human which has such cancer by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided is a method of monitoring colon cancer in a human having such cancer for the onset of metastasis. The method comprises identifying a human patient having such cancer that is not known to have metastasized; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of colon cancer in a human having such cancer by looking at levels of CSG in a human having such cancer. The method comprises identifying a human patient having such cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are methods of designing new therapeutic agents targeted to a CSG for use in imaging and treating colon cancer. For example, in one embodiment, therapeutic agents such as antibodies targeted against CSG or fragments of such antibodies can be used to treat, detect or image localization of CSG in a patient for the purpose of detecting or diagnosing a disease or condition. In this embodiment, an increase in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable and therapeutic labels including, but not limited to, radioisotopes and paramagnetic metals. Therapeutic agents such as small molecules and antibodies which decrease the concentration and/or activity of CSG can also be used in the treatment of diseases characterized by overexpression of CSG. Such agents can be readily identified in accordance with teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

GLOSSARY

The following illustrative explanations are provided to facilitate understanding of certain terms used frequently herein, particularly in the examples. The explanations are provided as a convenience and are not limitative of the invention.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. When introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

POLYNUCLEOTIDE(S) generally refers to any polyribonucleotide or polydeoxribonucleotide and is inclusive of unmodified RNA or DNA as well as modified RNA or DNA. Thus, for instance, polynucleotides as used herein refers to, among other things, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide, as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide is also inclusive of DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Modifications which may be present in polypeptides of the present invention include, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications including, but not limited to, glycosylation, lipid attachment, sulfation, gamma-carboxylation of glutamic acid residues, hydroxylation and ADP-ribosylation are described in most basic texts, such as, for instance PROTEINS STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated that the polypeptides of the present invention are not always entirely linear. Instead, polypeptides may be branched as a result of ubiquitination, and they may be circular, with or without branching, generally as a result of posttranslation events including natural processing event and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini. In fact, blockage of the amino and/or carboxyl group in a polypeptide by a covalent modification is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications, in large part, will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out the same posttranslational glycosylations as mammalian cells. Thus, insect cell expression systems have been developed to express efficiently mammalian proteins having native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively.

With respect to variant polynucleotides, differences are generally limited so that the nucleotide sequences of the reference and the variant are closely similar overall and, in many regions, identical. Thus, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Alternatively, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence.

With respect to variant polypeptides, differences are generally limited so that the sequences of the reference and the variant are closely similar overall and, in many region, identical. For example, a variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with CSG polypeptides of the present invention and is inclusive not only of classic receptors, which are preferred, but also other molecules that specifically bind to or interact with polypeptides of the invention (which also may be referred to as "binding molecules" and "interaction molecules," respectively and as "CSG binding or interaction molecules". Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind to polypeptides of the invention.

DETAILED DESCRIPTION OF THE INVENTION

The present invention relates to novel colon specific polypeptides and polynucleotides, referred to herein as CSGs, among other things, as described in greater detail below.

Polynucleotides

In accordance with one aspect of the present invention, there are provided isolated CSG polynucleotides which encode CSG polypeptides.

Using the information provided herein, such as the polynucleotide sequences set out in SEQ ID NO:1, 2, 3, 4, 5, 6, 7, 8, 9, 10, 11, 12, 13, 14, 15, 16, 17, 18, or 19, a polynucleotide of the present invention encoding a CSG may be obtained using standard cloning and screening procedures, such as those for cloning cDNAs using mRNA from cells of a human tumor as starting material.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptides may be identical to the coding sequence of the polynucleotides of SEQ ID NO:1, 2, 3, 4, 5, 6, 7, 8, 9, 10, 11, 12, 13, 14, 15, 16, 17, 18, or 19. It also may be a polynucleotide with a different sequence, which, as a result of the redundancy (degeneracy) of the genetic code, encodes the same polypeptides as encoded by SEQ ID NO:1, 2, 3, 4, 5, 6, 7, 8, 9, 10, 11, 12, 13, 14, 15, 16, 17, 18, or 19.

Polynucleotides of the present invention, such as SEQ ID NO: 1, 2, 3, 4, 5, 6, 7, 8, 9, 10, 11, 12, 13, 14, 15, 16, 17, 18, or 19 which encode these polypeptides may comprise the coding sequence for the mature polypeptide by itself. Polynucleotides of the present invention may also comprise the coding sequence for the mature polypeptide and additional coding sequences such as those encoding a leader or secretory sequence such as a pre-, or pro- or prepro-protein sequence. Polynucleotides of the present invention may also comprise the coding sequence of the mature polypeptide, with or without the aforementioned additional coding sequences, together with additional, non-coding sequences. Examples of additional non-coding sequences which may be incorporated into the polynucleotide of the present invention include, but are not limited to, introns and non-coding 5' and 3' sequences such as transcribed, non-translated sequences that play a role in transcription, mRNA processing including, for example, splicing and polyadenylation signals, ribosome binding and stability of mRNA, and additional coding sequence which codes for amino acids such as those which provide additional functionalities. Thus, for instance, the polypeptide may be fused to a marker sequence such as a peptide which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al. (Proc. Natl. Acad. Sci., USA 86: 821–824 (1989)), for instance, hexa-histidine provides for convenient purification of the fusion protein. The HA tag corresponds to an epitope derived of influenza hemagglutinin protein (Wilson et al., Cell 37: 767 (1984)).

In accordance with the foregoing, the term "polynucleotide encoding a polypeptide" as used herein encompasses polynucleotides which include a sequence encoding a polypeptide of the present invention, particularly SEQ ID NO:1, 2, 3, 4, 5, 6, 7, 8, 9, 10, 11, 12, 13, 14, 15, 16, 17, 18 or 19. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the CSG polypeptides. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the same amino acid sequence encoded by a CSG polynucleotide comprising SEQ ID NO: 1, 2, 3, 4, 5, 6, 7, 8, 9, 10, 11, 12, 13, 14, 15, 16, 17, 18 or 19; variants, analogs, derivatives and fragments thereof, and fragments of the variants, analogs and derivatives. Further particularly preferred in this regard are CSG polynucleotides encoding polypeptide variants, analogs, derivatives and fragments, and variants, analogs and derivatives of the fragments, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the CSG. Also especially preferred in this regard are conservative substitutions. Most highly preferred are polynucleotides encoding polypeptides having the amino acid sequences as polypeptides encoded by SEQ ID NO: 1, 2, 3, 4, 5, 6, 7, 8, 9, 10, 11, 12, 13, 14, 15, 16, 17, 18 or 19 without substitutions.

Further preferred embodiments of the invention are CSG polynucleotides that are at least 70% identical to a polynucleotide of SEQ ID NO: 1, 2, 3, 4, 5, 6, 7, 8, 9, 10, 11, 12, 13, 14, 15, 16, 17, 18, or 19 and polynucleotides which are complementary to such polynucleotides. More preferred are CSG polynucleotides that comprise a region that is at least 80% identical to a polynucleotide of SEQ ID NO: 1, 2, 3, 4, 5, 6, 7, 8, 9, 10, 11, 12, 13, 14, 15, 16, 17, 18 or 19. In this regard, CSG polynucleotides at least 90% identical to the same are particularly preferred, and among these particularly preferred CSG polynucleotides, those with at least 95% are especially preferred. Furthermore, those with at least 97% are highly preferred among those with at least 95%, and among these those with at least 98% and at least 99% are particularly highly preferred, with at least 99% being the most preferred.

Particularly preferred embodiments in this respect, moreover, are polynucleotides which encode polypeptides which retain substantially the same biological function or activity as the mature polypeptides encoded by a polynucleotide of SEQ ID NO: 1, 2, 3, 4, 5, 6, 7, 8, 9, 10, 11, 12, 13, 14, 15, 16, 17, 18 or 19.

The present invention further relates to polynucleotides that hybridize to the herein above-described CSG sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as described herein, may be used as a hybridization probe for cDNA and genomic DNA to isolate full-length cDNAs and genomic clones encoding CSGs and to isolate cDNA and genomic clones of other genes that have a high sequence similarity to these CSGs. Such probes generally will comprise at least 15 bases. Preferably, such probes will have at least 30 bases and may have at least 50 bases.

For example, the coding region of CSG of the present invention may be isolated by screening using an oligonucleotide probe synthesized from the known DNA sequence. A labeled oligonucleotide having a sequence complementary to that of a gene of the present invention is used to screen a library of human cDNA, genomic DNA or mRNA to determine which members of the library the probe hybridizes with.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate/protein trafficking, may prolong or shorten protein half-life or may facilitate manipulation of a protein for assay or production, among other things. As generally is the case in situ, the additional amino acids may be processed away from the mature protein by cellular enzymes.

A precursor protein having the mature form of the polypeptide fused to one or more prosequences may be an inactive form of the polypeptide. When prosequences are removed, such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to CSG polypeptides, preferably polypeptides encoded by a polynucleotide of SEQ ID NO: 1, 2, 3, 4, 5, 6, 7, 8, 9, 10, 11, 12, 13, 14, 15, 16, 17, 18, or 19. The invention also relates to fragments, analogs and derivatives of these polypeptides. The terms "fragment," "derivative" and "analog" when referring to the polypeptides of the present invention means a polypeptide which retains essentially the same biological function or activity as such polypeptides. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of a polypeptide of or the present invention may be (I) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

The polypeptides and polynucleotides of the present invention are preferably provided in an isolated form, and preferably are purified to homogeneity.

The polypeptides of the present invention include the polypeptides encoded by the polynucleotide of SEQ ID NO: 1, 2, 3, 4, 5, 6, 7, 8, 9, 10, 11, 12, 13, 14, 15, 16, 17, 18 or 19 (in particular the mature polypeptide) as well as polypeptides which have at least 75% similarity (preferably at least 75% identity), more preferably at least 90% similarity (more preferably at least 90% identity), still more preferably at least 95% similarity (still more preferably at least 95% identity), to a polypeptide encoded by SEQ ID NO: 1, 2, 3, 4, 5, 6, 7, 8, 9, 10, 11, 12, 13, 14, 15, 16, 17, 18 or 19. Also included are portions of such polypeptides generally containing at least 30 amino acids and more preferably at least 50 amino acids.

As known in the art "similarity" between two polypeptides is determined by comparing the amino acid sequence and its conserved amino acid substitutes of one polypeptide sequence with that of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of a polypeptide encoded by a polynucleotide of SEQ ID NO: 1, 2, 3, 4, 5, 6, 7, 8, 9, 10, 11, 12, 13, 14, 15, 16, 17, 18, or 19. In this regard a fragment is a polypeptide having an amino acid sequence that entirely is the same as part but not all of the amino acid sequence of the aforementioned CSG polypeptides and variants or derivatives thereof.

Such fragments may be "free-standing," i.e., not part of or fused to other amino acids or polypeptides, or they may be contained within a larger polypeptide of which they form a part or region. When contained within a larger polypeptide, the presently discussed fragments most preferably form a single continuous region. However, several fragments may be comprised within a single larger polypeptide. For instance, certain preferred embodiments relate to a fragment of a CSG polypeptide of the present comprised within a precursor polypeptide designed for expression in a host and having heterologous pre- and pro-polypeptide regions fused to the amino terminus of the CSG fragment and an additional region fused to the carboxyl terminus of the fragment. Therefore, fragments in one aspect of the meaning intended herein, refers to the portion or portions of a fusion polypeptide or fusion protein derived from a CSG polypeptide.

As representative examples of polypeptide fragments of the invention, there may be mentioned those which have from about 15 to about 139 amino acids. In this context "about" includes the particularly recited range and ranges larger or smaller by several, a few, 5, 4, 3, 2 or 1 amino acid at either extreme or at both extremes. Highly preferred in this regard are the recited ranges plus or minus as many as 5 amino acids at either or at both extremes. Particularly highly preferred are the recited ranges plus or minus as many as 3 amino acids at either or at both the recited extremes. Especially preferred are ranges plus or minus 1 amino acid at either or at both extremes or the recited ranges with no additions or deletions. Most highly preferred of all in this regard are fragments from about 15 to about 45 amino acids.

Among especially preferred fragments of the invention are truncation mutants of the CSG polypeptides. Truncation mutants include CSG polypeptides having an amino acid sequence encoded by a polynucleotide of SEQ ID NO: 1, 2, 3, 4, 5, 6, 7, 8, 9, 10, 11, 12, 13, 14, 15, 16, 17, 18 or 19, or variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out herein also are preferred embodiments of truncation fragments, which are especially preferred among fragments generally.

Also preferred in this aspect of the invention are fragments characterized by structural or functional attributes of the CSG polypeptides of the present invention. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of the CSG polypeptides of the present invention. Regions of the aforementioned types are identified routinely by analysis of the amino acid sequences encoded by the polynucleotides of SEQ ID NO: 1, 2, 3, 4, 5, 6, 7, 8, 9, 10, 11, 12, 13, 14, 15, 16, 17, 18 or 19. Preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions. Among highly preferred fragments in this regard are those that comprise regions of CSGs that combine several structural features, such as several of the features set out above. In this regard, the regions defined by selected residues of a CSG polypeptide which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of CSG polypeptides. Most highly preferred in this regard are fragments that have a chemical, biological or other activity of a CSG polypeptide, including those with a similar activity or an improved activity, or with a decreased undesirable activity. Highly preferred in this regard are fragments that contain regions that are homologs in sequence, or in position, or in both sequence and to active regions of related polypeptides, and which include colon specific-binding proteins. Among particularly preferred fragments in these regards are truncation mutants, as discussed above.

It will be appreciated that the invention also relates to polynucleotides encoding the aforementioned fragments, polynucleotides that hybridize to polynucleotides encoding the fragments, particularly those that hybridize under stringent conditions, and polynucleotides such as PCR primers for amplifying polynucleotides that encode the fragments. In these regards, preferred polynucleotides are those that correspond to the preferred fragments, as discussed above.

Fusion Proteins

In one embodiment of the present invention, the CSG polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See also EP A 394,827; Traunecker, et al., Nature 331: 84–86 (1988)) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of these types of fusion proteins described above can be made in accordance with well known protocols.

For example, a CSG polypeptide can be fused to an IgG molecule via the following protocol. Briefly, the human Fc portion of the IgG molecule is PCR amplified using primers that span the 5' and 3' ends of the sequence. These primers also have convenient restriction enzyme sites that facilitate cloning into an expression vector, preferably a mammalian expression vector. For example, if pC4 (Accession No. 209646) is used, the human Fc portion can be ligated into the BamHI cloning site. In this protocol, the 3' BamHI site must be destroyed. Next, the vector containing the human Fc portion is re-restricted with BamHI thereby linearizing the vector, and a CSG polynucleotide of the present invention is ligated into this BamHI site. It is preferred that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Diagnostic Assays

The present invention also relates to diagnostic assays and methods, both quantitative and qualitative for detecting, diagnosing, monitoring, staging and prognosticating cancers by comparing levels of CSG in a human patient with those of CSG in a normal human control. For purposes of the present invention, what is meant by CSG levels is, among other things, native protein expressed by a gene comprising the polynucleotide sequence of SEQ ID NO: 1, 2, 3, 4, 5, 6, 7, 8, 9, 10, 11, 12, 13, 14, 15, 16, 17, 18 or 19. By "CSG" it is also meant herein polynucleotides which, due to degeneracy in genetic coding, comprise variations in nucleotide sequence as compared to SEQ ID NO: 1, 2, 3, 4, 5, 6, 7, 8, 9, 10, 11, 12, 13, 14, 15, 16, 17, 18 or 19 but which still encode the same protein. The native protein being detected may be whole, a breakdown product, a complex of molecules or chemically modified. In the alternative, what is meant by CSG as used herein, means the native mRNA encoded by a polynucleotide sequence of SEQ ID NO: 1, 2, 3, 4, 5, 6, 7, 8, 9, 10, 11, 12, 13, 14, 15, 16, 17, 18 or 19, levels of the gene comprising the polynucleotide sequence of SEQ ID NO: 1, 2, 3, 4, 5, 6, 7, 8, 9, 10, 11, 12, 13, 14, 15, 16, 17, 18 or 19 or levels of a polynucleotide which is capable of hybridizing under stringent conditions to the antisense sequence of SEQ ID NO: 1, 2, 3, 4, 5, 6, 7, 8, 9, 10, 11, 12, 13, 14, 15, 16, 17, 18 or 19. Such levels are preferably determined in at least one of cells, tissues and/or bodily fluids, including determination of normal and abnormal levels. Thus, for instance, a diagnostic assay in accordance with the invention for diagnosing overexpression of CSG protein compared to normal control bodily fluids, cells, or tissue samples may be used to diagnose the presence of colon cancer.

All the methods of the present invention may optionally include determining the levels of other cancer markers as well as CSG. Other cancer markers, in addition to CSG, useful in the present invention will depend on the cancer being tested and are known to those of skill in the art.

The present invention provides methods for diagnosing the presence of colon cancer by analyzing for changes in levels of CSG in cells, tissues or bodily fluids compared with levels of CSG in cells, tissues or bodily fluids of preferably the same type from a normal human control, wherein an increase in levels of CSG in the patient versus the normal human control is associated with the presence of colon cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastatic colon cancer in a patient having colon cancer which has not yet metastasized for the onset of metastasis. In the method of the present invention, a human cancer patient suspected of having colon cancer which may have metastasized (but which was not previously known to have metastasized) is identified. This is accomplished by a variety of means known to those of skill in the art.

In the present invention, determining the presence of CSG levels in cells, tissues or bodily fluid, is particularly useful for discriminating between colon cancer which has not metastasized and colon cancer which has metastasized. Existing techniques have difficulty discriminating between colon cancer which has metastasized and colon cancer which has not metastasized and proper treatment selection is often dependent upon such knowledge.

In the present invention, the cancer marker levels measured in such cells, tissues or bodily fluid is CSG, and are compared with levels of CSG in preferably the same cells, tissue or bodily fluid type of a normal human control. That is, if the cancer marker being observed is just CSG in serum, this level is preferably compared with the level of CSG in serum of a normal human control. An increase in the CSG in the patient versus the normal human control is associated with colon cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have colon cancer which has not metastasized.

Staging

The invention also provides a method of staging colon cancer in a human patient. The method comprises identifying a human patient having such cancer and analyzing cells, tissues or bodily fluid from such human patient for CSG. The CSG levels determined in the patient are then compared with levels of CSG in preferably the same cells, tissues or bodily fluid type of a normal human control, wherein an increase in CSG levels in the human patient versus the normal human control is associated with a cancer which is progressing and a decrease in the levels of CSG (but still increased over true normal levels) is associated with a cancer which is regressing or in remission.

Monitoring

Further provided is a method of monitoring colon cancer in a human patient having such cancer for the onset of metastasis. The method comprises identifying a human patient having such cancer that is not known to have metastasized; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which has metastasized. In this method, normal human control samples may also include prior patient samples.

Further provided by this invention is a method of monitoring the change in stage of colon cancer in a human patient having such cancer. The method comprises identifying a human patient having such cancer; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which is progressing in stage and a decrease in the levels of CSG is associated with a cancer which is regressing in stage or in remission. In this method, normal human control samples may also include prior patient samples.

Monitoring a patient for onset of metastasis is periodic and preferably done on a quarterly basis. However, this may be done more or less frequently depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of CSG. The present invention provides a method in which a test sample is obtained from a human patient and CSG is detected. The presence of higher CSG levels as compared to normal human controls is diagnostic for the human patient being at risk for developing cancer, particularly colon cancer.

The effectiveness of therapeutic agents to decrease expression or activity of the CSGs of the invention can also be monitored by analyzing levels of expression of the CSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in CSG, thereby determining if a human with the genetic lesion is at risk for colon cancer or has colon cancer. Genetic lesions can be detected, for example, by ascertaining the existence of a deletion and/or addition and/or substitution of one or more nucleotides from the CSGs of this invention, a chromosomal rearrangement of CSG, aberrant modification of CSG (such as of the methylation pattern of the genomic DNA), the presence of a non-wild type splicing pattern of a mRNA transcript of CSG, allelic loss of CSG, and/or inappropriate post-translational modification of CSG protein. Methods to detect such lesions in the CSG of this invention are known to those of skill in the art.

For example, in one embodiment, alterations in a gene corresponding to a CSG polynucleotide of the present invention are determined via isolation of RNA from entire families or individual patients presenting with a phenotype of interest (such as a disease) is be isolated. cDNA is then generated from these RNA samples using protocols known in the art. See, e.g. Sambrook et al. (MOLECULAR CLONING: A LABORATORY MANUAL, 2nd Ed., Cold Spring Harbor Laboratory Press, Cold Spring Harbor, N.Y. (1989)), which is illustrative of the many laboratory manuals that detail these techniques. The cDNA is then used as a template for PCR, employing primers surrounding regions of interest in SEQ ID NO: 1, 2, 3, 4, 5, 6, 7, 8, 9, 10, 11, 12, 13, 14, 15, 16, 17, 18 or 19. PCR conditions typically consist of 35 cycles at 95° C. for 30 seconds; 60–120 seconds at 52–58° C.; and 60–120 seconds at 70° C., using buffer solutions described in Sidransky, D., et al., Science 252: 706 (1991). PCR products are sequenced using primers labeled at their 5' end with T4 polynucleotide kinase, employing SequiTherm Polymerase (Epicentre Technologies). The intron-exon borders of selected exons are also determined and genomic PCR products analyzed to confirm the results. PCR products harboring suspected mutations are then cloned and sequenced to validate the results of the direct sequencing. PCR products are cloned into T-tailed vectors as described in Holton, T. A. and Graham, M. W., Nucleic Acids Research, 19: 1156 (1991) and sequenced with T7 polymerase (United States Biochemical). Affected individuals are identified by mutations not present in unaffected individuals.

Genomic rearrangements can also be observed as a method of determining alterations in a gene corresponding to a polynucleotide. In this method, genomic clones are nick-translated with digoxigenin deoxy-uridine 5' triphosphate (Boehringer Manheim), and FISH is performed as described in Johnson, C. et al., Methods Cell Biol. 35: 73–99 (1991). Hybridization with a labeled probe is carried out using a vast excess of human DNA for specific hybridization to the corresponding genomic locus. Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters (Johnson et al., Genet. Anal. Tech. Appl., 8: 75 (1991)). Image collection, analysis and chromosomal fractional length measurements are performed using the ISee Graphical Program System (Inovision Corporation, Durham, N.C.). Chromosome alterations of the genomic region hybridized by the probe are identified as insertions, deletions, and translocations. These alterations are used as a diagnostic marker for an associated disease.

Assay Techniques

Assay techniques that can be used to determine levels of gene expression (including protein levels), such as CSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent, for example horseradish peroxidase enzyme or alkaline phosphatase.

To carry out the ELISA, antibody specific to CSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to a detectable reagent such as horseradish peroxidase is placed in the dish resulting in binding of the reporter antibody to any monoclonal antibody bound to CSG. Unattached reporter antibody is then washed out. Reagents for peroxidase activity, including a calorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay can also be employed wherein antibodies specific to CSG are attached to a solid support and labeled CSG and a sample derived from the host are passed over the solid support. The amount of label detected which is attached to the solid support can be correlated to a quantity of CSG in the sample.

Using all or a portion of a nucleic acid sequence of CSG of the present invention as a hybridization probe, nucleic acid methods can also be used to detect CSG mRNA as a marker for colon cancer. Polymerase chain reaction (PCR) and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to both detect the expression of and quantitate the level of expression of that gene. In this approach, a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels.

First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot.

Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of CSG/Colon Cancer Therapy

Identification of this CSG is also useful in the rational design of new therapeutics for imaging and treating cancers, and in particular colon cancer. For example, in one embodiment, antibodies which specifically bind to CSG can be raised and used in vivo in patients suspected of suffering from colon cancer. Antibodies which specifically bind CSG can be injected into a patient suspected of having colon cancer for diagnostic and/or therapeutic purposes. Thus, another aspect of the present invention provides for a method for preventing the onset and treatment of colon cancer in a human patient in need of such treatment by administering to the patient an effective amount of antibody. By "effective amount" it is meant the amount or concentration of antibody needed to bind to the target antigens expressed on the tumor to cause tumor shrinkage for surgical removal, or disappearance of the tumor. The binding of the antibody to the overexpressed CSG is believed to cause the death of the cancer cell expressing such CSG. The preparation and use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against CSG can be used in a similar manner. Labeled antibodies which specifically bind CSG can be injected into patients suspected of having colon cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence of the label, as compared to imaging of normal tissue, permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to CSG protein or have a modulatory effect on the expression or activity of CSG protein. Modulators which decrease the expression or activity of CSG protein are believed to be useful in treating colon cancer. Such screening assays are known to those of skill in the art and include, without limitation, cell-based assays and cell free assays.

Small molecules predicted via computer imaging to specifically bind to regions of CSG can also be designed, synthesized and tested for use in the imaging and treatment of colon cancer. Further, libraries of molecules can be screened for potential anticancer agents by assessing the ability of the molecule to bind to the CSGs identified herein. Molecules identified in the library as being capable of binding to CSG are key candidates for further evaluation for use in the treatment of colon cancer. In a preferred embodiment, these molecules will downregulate expression and/or activity of CSG in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676–1680).

The present invention relates to compositions and methods of adoptive immunotherapy for the prevention and/or treatment of primary and metastatic colon cancer in humans using macrophages sensitized to the antigenic CSG molecules, with or without non-covalent complexes of heat shock protein (hsp). Antigenicity or immunogenicity of the CSG is readily confirmed by the ability of the CSG protein or a fragment thereof to raise antibodies or educate naive effector cells, which in turn lyse target cells expressing the antigen (or epitope).

Cancer cells are, by definition, abnormal and contain proteins which should be recognized by the immune system as foreign since they are not present in normal tissues. However, the immune system often seems to ignore this abnormality and fails to attack tumors. The foreign CSG proteins that are produced by the cancer cells can be used to reveal their presence. The CSG is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCs) are stimulated outside the body (ex vivo), using the tumor specific CSG antigen. The stimulated cells are then reinfused into the patient where they attack the cancerous cells. Research has shown that using both cytotoxic and helper T cells is far more effective than using either subset alone. Additionally, the CSG antigen may be complexed with heat shock proteins to stimulate the APCs as described in U.S. Pat. No. 5,985,270.

The APCs can be selected from among those antigen presenting cells known in the art including, but not limited to, macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the CSG can be introduced into effector cells similarly as in conventional gene therapy. This can enhance the cytotoxicity of the effector cells to tumor cells as they have been manipulated to produce the antigenic protein resulting in improvement of the adoptive immunotherapy.

CSG antigens of this invention are also useful as components of colon cancer vaccines. The vaccine comprises an immunogenically stimulatory amount of a CSG antigen. Immunogenically stimulatory amount refers to that amount of antigen that is able to invoke the desired immune response in the recipient for the amelioration, or treatment of colon cancer. Effective amounts may be determined empirically by standard procedures well known to those skilled in the art.

The CSG antigen may be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate CSG polynucleotides and express CSG polypeptides of the present invention. For instance, CSG polynucleotides may be introduced into host cells using well known techniques of infection, transduction, transfection, transvection and transformation. The CSG polynucleotides may be introduced alone or with other polynucleotides. Such other polynucleotides may be introduced independently, co-introduced or introduced joined to the CSG polynucleotides of the invention.

For example, CSG polynucleotides of the invention may be transfected into host cells with another, separate, polynucleotide encoding a selectable marker, using standard techniques for co-transfection and selection in, for instance, mammalian cells. In this case, the polynucleotides generally will be stably incorporated into the host cell genome.

Alternatively, the CSG polynucleotide may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce CSG polynucleotides into a host. If the vector is a virus, it may be packaged in vitro or introduced into a packaging cell and the packaged virus may be transduced into cells. A wide variety of well known techniques conducted routinely by those of skill in the art are suitable for making CSG polynucleotides and for introducing CSG polynucleotides into cells in accordance with this aspect of the invention. Such techniques are reviewed at length in reference texts such as Sambrook et al., previously cited herein.

Vectors which may be used in the present invention include, for example, plasmid vectors, single- or double-stranded phage vectors, and single- or double-stranded RNA or DNA viral vectors. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case viral propagation generally will occur only in complementing host cells.

Preferred vectors for expression of polynucleotides and polypeptides of the present invention include, but are not limited to, vectors comprising cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced to express by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media which may be modified as appropriate for, inter alia, activating promoters, selecting transformants or amplifying genes. Culture conditions such as temperature, pH and the like, previously used with the host cell selected for expression, generally will be suitable for expression of CSG polypeptides of the present invention.

A great variety of expression vectors can be used to express CSG polypeptides of the invention. Such vectors include chromosomal, episomal and virus-derived vectors. Vectors may be derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and from combinations thereof such as those derived from plasmid and bacteriophage genetic elements, such as cosmids and phagemids. All may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representative promoters include the phage lambda PL promoter, the *E. coli* lac, trp and tac promoters, the SV40 early and late promoters, and promoters of retroviral LTRs, to name just a few of the well-known promoters. It will be understood that numerous promoters not mentioned are also suitable for use in this aspect of the invention and are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing in *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a CSG polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such CSG sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated by those of skill in the art upon reading this disclosure that any other plasmid or vector suitable for introduction, maintenance, propagation and/or expression of a CSG polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of a restriction site or sites for introducing a candidate promoter fragment; i.e., a fragment that may contain a promoter. As is well known, introduction into the vector of a promoter-containing fragment at the restriction site upstream of the cat gene engenders production of CAT activity detectable by standard CAT assays. Vectors suitable to this end are well known and readily available. Two such vectors are pKK232-8 and pCM7. Thus, promoters for expression of CSG polynucleotides of the present invention include, not only well known and readily available promoters, but also promoters that readily may be obtained by the foregoing technique, using a reporter gene.

Among known bacterial promoters suitable for expression of polynucleotides and polypeptides in accordance with the present invention are the *E. coli* laci and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs. The host cell can be a higher eukaryotic cell, such as a mammalian cell, or a lower eukaryotic cell, such as a yeast cell. Alternatively, the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, CSG polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al. cited elsewhere herein.

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trpl gene of *S. cerevisiae*.

Transcription of DNA encoding the CSG polypeptides of the present invention by higher eukaryotes may be increased by inserting an enhancer sequence into the vector. Enhancers are cis-acting elements of DNA, usually about from 10 to 300 base pairs (bp) that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the present invention, encoding a heterologous structural sequence of a CSG polypeptide of the present invention, generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, lying between the ribosome binding site and the initiating AUG. Also, generally, there will be a translation stop codon at the end of the polypeptide and there will be a polyadenylation signal and a transcription termination signal appropriately disposed at the 3' end of the transcribed region.

Appropriate secretion signals may be incorporated into the expressed polypeptide for secretion of the translated protein into the lumen of the endoplasmic reticulum, into the periplasmic space or into the extracellular environment. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell during purification or during subsequent handling and storage. A region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of CSG polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Many other hosts also known to those of skill may also be employed in this regard.

As a representative, but non-limiting example, useful expression vectors for bacterial use can comprise a selectable marker and bacterial origin of replication derived from commercially available plasmids comprising genetic elements of the well known cloning vector pBR322. Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, where the selected promoter is inducible it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. An exemplary mammalian expression systems is the COS-7 line of monkey kidney fibroblasts described in Gluzman et al., Cell 23: 175 (1981). Other mammalian cell lines capable of expressing a compatible vector include for example, the C127, 3T3, CHO, HeLa, human kidney 293 and BHK cell lines. Mammalian expression vectors comprise an origin of replication, a suitable promoter and enhancer, and any ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

CSG polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

CSG polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the CSG polypeptides of the present invention may be glycosylated or may be non-glycosylated. In addition, CSG polypeptides of the invention may also include an initial modified methionine residue, in some cases as a result of host-mediated processes.

CSG polynucleotides and polypeptides may be used in accordance with the present invention for a variety of applications, particularly those that make use of the chemical and biological properties of the CSGS. Additional applications relate to diagnosis and to treatment of disorders of cells, tissues and organisms. These aspects of the invention are illustrated further by the following discussion.

Polynucleotide Assays

As discussed in some detail supra, this invention is also related to the use of CSG polynucleotides to detect complementary polynucleotides such as, for example, as a diagnostic reagent. Detection of a mutated form of CSG associated with a dysfunction will provide a diagnostic tool that can add to or define a diagnosis of a disease or susceptibility to a disease which results from under-expression, over-expression or altered expression of a CSG, such as, for example, a susceptibility to inherited colon cancer.

Individuals carrying mutations in a human CSG gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically using PCR prior to analysis(Saiki et al., Nature, 324: 163–166 (1986)). RNA or cDNA may also be used in a similar manner. As an example, PCR primers complementary to a CSG polynucleotide of SEQ ID NO: 1, 2, 3, 4, 5, 6, 7, 8, 9, 10, 11, 12, 13, 14, 15, 16, 17, 18 or 19 can be used to identify and analyze CSG expression and mutations. For example, deletions and insertions can be detected by a change in size of the amplified product in comparison to the normal genotype. Point mutations can be identified by hybridizing amplified DNA to radiolabeled CSG RNA or alternatively, radiolabeled CSG antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA. In addition to more conventional gel-electrophoresis and DNA sequencing, mutations also can be detected by in situ analysis.

Chromosome Assays

The CSG sequences of the present invention are also valuable for chromosome identification. There is a need for identifying particular sites on the chromosome and few chromosome marking reagents based on actual sequence data (repeat polymorphisms) are presently available for marking chromosomal location. Each CSG sequence of the present invention is specifically targeted to and can hybridize with a particular location on an individual human chromosome. Thus, the CSGs can be used in the mapping of DNAs to chromosomes, an important first step in correlating sequences with genes associated with disease.

In certain preferred embodiments in this regard, the cDNA herein disclosed is used to clone genomic DNA of a CSG of the present invention. This can be accomplished using a variety of well known techniques and libraries, which generally are available commercially. The genomic DNA is used for in situ chromosome mapping using well known techniques for this purpose.

In some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60 bp. This technique is described by Verma et al. (HUMAN CHROMOSOMES: A MANUAL OF BASIC TECHNIQUES, Pergamon Press, New York (1988)).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

As described in some detail supra, the present invention also relates to diagnostic assays such as quantitative and diagnostic assays for detecting levels of CSG polypeptide in cells and tissues, and biological fluids such as blood and urine, including determination of normal and abnormal levels. Thus, for instance, a diagnostic assay in accordance with the present invention for detecting over-expression or under-expression of a CSG polypeptide compared to normal control tissue samples may be used to detect the presence of neoplasia. Assay techniques that can be used to determine levels of a protein, such as a CSG polypeptide of the present invention, in a sample derived from a host are well-known to those of skill in the art. Such assay methods include radioimmunoassays, competitive-binding assays, Western Blot analysis and ELISA assays. Among these ELISAs frequently are preferred.

For example, antibody-sandwich ELISAs are used to detect polypeptides in a sample, preferably a biological sample. Wells of a microtiter plate are coated with specific antibodies, at a final concentration of 0.2 to 10 $\mu$g/ml. The antibodies are either monoclonal or polyclonal and are produced by methods as described herein. The wells are blocked so that non-specific binding of the polypeptide to the well is reduced. The coated wells are then incubated for >2 hours at room temperature with a sample containing the CSG polypeptide. Preferably, serial dilutions of the sample should be used to validate results. The plates are then washed three times with deionized or distilled water to remove unbounded polypeptide. Next, 50 $\mu$l of specific antibody-alkaline phosphatase conjugate, at a concentration of 25–400 ng, is added and incubated for 2 hours at room temperature. The plates are again washed three times with deionized or distilled water to remove unbounded conjugate. 4-methylumbelliferyl phosphate (MUP) or p-nitrophenyl phosphate (NPP) substrate solution (75 $\mu$l) is then added to each well and the plate is incubated 1 hour at room temperature. The reaction is measured by a microtiter plate reader. A standard curve is prepared using serial dilutions of a control sample, and polypeptide concentration is plotted on the X-axis (log scale) while fluorescence or absorbance is plotted on the Y-axis (linear scale). The concentration of the CSG polypeptide in the sample is interpolated using the standard curve.

Antibodies

As discussed in some detail supra, CSG polypeptides, their fragments or other derivatives, or analogs thereof, or cells expressing them can be used as an immunogen to produce antibodies thereto. These antibodies can be polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

A variety of methods for antibody production are set forth in Current Protocols, Chapter 2.

For example, cells expressing a CSG polypeptide of the present invention can be administered to an animal to induce the production of sera containing polyclonal antibodies. In a preferred method, a preparation of the secreted protein is prepared and purified to render it substantially free of natural contaminants. This preparation is then introduced into an animal in order to produce polyclonal antisera of greater specific activity. The antibody obtained will bind with the CSG polypeptide itself. In this manner, even a sequence encoding only a fragment of the CSG polypeptide can be used to generate antibodies binding the whole native polypeptide. Such antibodies can then be used to isolate the CSG polypeptide from tissue expressing that CSG polypeptide.

Alternatively, monoclonal antibodies can be prepared. Examples of techniques for production of monoclonal antibodies include, but are not limited to, the hybridoma technique (Kohler, G. and Milstein, C., Nature 256: 495–497 (1975), the trioma technique, the human B-cell hybridoma technique (Kozbor et al., Immunology Today 4: 72 (1983) and (Cole et al., pg. 77–96 in MONOCLONAL ANTIBODIES AND CANCER THERAPY, Alan R. Liss, Inc. (1985). The EBV-hybridoma technique is useful in production of human monoclonal antibodies.

Hybridoma technologies have also been described by Khler et al. (Eur. J. Immunol. 6: 511 (1976)) Khler et al. (Eur. J. Immunol. 6: 292 (1976)) and Hammerling et al. (in: Monoclonal Antibodies and T-Cell Hybridomas, Elsevier, N.Y., pp. 563–681 (1981)). In general, such procedures involve immunizing an animal (preferably a mouse) with CSG polypeptide or, more preferably, with a secreted CSG polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80: 225–232 (1981).). The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein specific antibody and can be used to immunize an animal to induce formation of further protein-specific antibodies.

Techniques described for the production of single chain antibodies (U.S. Pat. No. 4,946,778) can also be adapted to produce single chain antibodies to immunogenic polypeptide products of this invention. Also, transgenic mice, as well as other nonhuman transgenic animals, may be used to express humanized antibodies to immunogenic polypeptide products of this invention.

It will be appreciated that Fab, F(ab')2 and other fragments of the antibodies of the present invention may also be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (See, for review, Morrison, Science 229: 1202 (1985); Oi et al., BioTechniques 4: 214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312: 643 (1984); Neuberger et al., Nature 314: 268 (1985).)

The above-described antibodies may be employed to isolate or to identify clones expressing CSG polypeptides or purify CSG polypeptides of the present invention by attachment of the antibody to a solid support for isolation and/or purification by affinity chromatography. As discussed in more detail supra, antibodies specific against a CSG may also be used to image tumors, particularly cancer of the colon, in patients suffering from cancer. Such antibodies may also be used therapeutically to target tumors expressing a CSG.

CSG Binding Molecules and Assays

This invention also provides a method for identification of molecules, such as receptor molecules, that bind CSGs. Genes encoding proteins that bind CSGs, such as receptor proteins, can be identified by numerous methods known to those of skill in the art. Examples include, but are not limited to, ligand panning and FACS sorting. Such methods are described in many laboratory manuals such as, for instance, Coligan et al., Current Protocols in Immunology 1(2): Chapter 5 (1991).

Expression cloning may also be employed for this purpose. To this end, polyadenylated RNA is prepared from a cell responsive to a CSG of the present invention. A cDNA library is created from this RNA and the library is divided into pools. The pools are then transfected individually into cells that are not responsive to a CSG of the present invention. The transfected cells then are exposed to labeled CSG. CSG polypeptides can be labeled by a variety of well-known techniques including, but not limited to, standard methods of radio-iodination or inclusion of a recognition site for a site-specific protein kinase. Following exposure, the cells are fixed and binding of labeled CSG is determined. These procedures conveniently are carried out on glass slides. Pools containing labeled CSG are identified as containing cDNA that produced CSG-binding cells. Subpools are then prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess CSG binding capacity of CSG binding molecules, such as receptor molecules, in cells or in cell-free preparations.

Agonists and Antagonists—Assays and Molecules

The invention also provides a method of screening compounds to identify those which enhance or block the action of a CSG on cells. By "compound", as used herein, it is meant to be inclusive of small organic molecules, peptides, polypeptides and antibodies as well as any other candidate molecules which have the potential to enhance or agonize or block or antagonize the action of CSG on cells. As used herein, an agonist is a compound which increases the natural biological functions of a CSG or which functions in a manner similar to a CSG, while an antagonist, as used herein, is a compound which decreases or eliminates such functions. Various known methods for screening for agonists and/or antagonists can be adapted for use in identifying CSG agonist or antagonists.

For example, a cellular compartment, such as a membrane or a preparation thereof, such as a membrane-preparation, may be prepared from a cell that expresses a molecule that binds a CSG, such as a molecule of a signaling or regulatory pathway modulated by CSG. The preparation is incubated with labeled CSG in the absence or the presence of a compound which may be a CSG agonist or antagonist. The ability of the compound to bind the binding molecule is reflected in decreased binding of the labeled ligand. Compounds which bind gratuitously, i.e., without inducing the effects of a CSG upon binding to the CSG binding molecule are most likely to be good antagonists. Compounds that bind well and elicit effects that are the same as or closely related to CSG are agonists. CSG-like effects of potential agonists and antagonists may by measured, for instance, by determining activity of a second messenger system following interaction of the candidate molecule with a cell or appropriate cell preparation, and comparing the effect with that of CSG or molecules that elicit the same effects as CSG. Second messenger systems that may be useful in this regard include, but are not limited to, AMP guanylate cyclase, ion channel or phosphoinositide hydrolysis second messenger systems.

Another example of an assay for CSG antagonists is a competitive assay that combines CSG and a potential antagonist with membrane-bound CSG receptor molecules or recombinant CSG receptor molecules under appropriate conditions for a competitive inhibition assay. CSG can be labeled, such as by radioactivity, such that the number of CSG molecules bound to a receptor molecule can be determined accurately to assess the effectiveness of the potential antagonist.

Potential antagonists include small organic molecules, peptides, polypeptides and antibodies that bind to a CSG polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing CSG-induced activities, thereby preventing the action of CSG by excluding CSG from binding.

Potential antagonists include small molecules which bind to and occupy the binding site of the CSG polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); OLIGODEOXYNUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes a mature CSG polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of a CSG polypeptide. The antisense RNA oligonucleotide hybridizes to the mRNA in vivo and blocks translation of the mRNA molecule into a CSG polypeptide. The oligonucleotides described above can also be delivered to cells such that the antisense RNA or DNA may be expressed in vivo to inhibit production of a CSG.

Compositions

The present invention also relates to compositions comprising a CSG polynucleotide or a CSG polypeptide or an agonist or antagonist thereof.

For example, a CSG polynucleotide, polypeptide or an agonist or antagonist thereof of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Compositions of the present invention will be formulated and dosed in a fashion consistent with good medical practice, taking into account the clinical condition of the individual patient (especially the side effects of treatment with the polypeptide or other compound alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1, $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the polypeptide or other compound is typically administered at a dose rate of about 1 $\mu$g/kg/hour to about 50 mg/kg/hour, either by 1–4 injections per day or by continuous subcutaneous infusion, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The polypeptide or other compound is also suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773,919 and EP 58481), copolymers of L-glutamic acid and gamma-ethyl-L-glutamate (Sidman, U. et al., Biopolymers 22: 547–556 (1983)), poly (2-hydroxyethyl methacrylate) (R. Langer et al., J. Biomed. Mater. Res. 15: 167–277 (1981), and R. Langer, Chem. Tech. 12: 98–105 (1982)), ethylene vinyl acetate (R. Langer et al.) and poly-D-(–)-3-hydroxybutyric acid (EP 133,988). Sustained-release compositions also include liposomally entrapped polypeptides. Liposomes containing the polypeptide or other compound are prepared by well known methods (Epstein et al., Proc. Natl. Acad. Sci. USA 82: 3688–3692 (1985); Hwang et al., Proc. Natl. Acad. Sci. USA 77: 4030–4034 (1980); EP 52322; EP 36676; EP 88046; EP 143949; EP 142641; Japanese Pat. Appl. 83-118008; U.S. Pat. Nos. 4,485,045 and 4,544,545; and EP 102324). Ordinarily, the liposomes are of the small (about 200–800 Angstroms) unilamellar type in which the lipid content is greater than about 30 mol. percent cholesterol, the selected proportion being adjusted for the optimal therapy.

For parenteral administration, in one embodiment, the polypeptide or other compound is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

For example, the formulation preferably does not include oxidizing agents and other compounds that are known to be deleterious to the polypeptide or other compound.

Generally, the formulations are prepared by contacting the polypeptide or other compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The polypeptide or other compound is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts or salts of the other compounds.

Any polypeptide to be used for therapeutic administration should be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

CSG polypeptides or polynucleotides or other compounds, preferably agonists or antagonists thereof of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. However, it will be appreciated that optimum dosage will be determined by standard methods for each treatment modality and indication, taking into account the indication, its severity, route of administration, complicating conditions and the like.

It will be appreciated that conditions caused by a decrease in the standard or normal expression level of a CSG polypeptide in an individual can be treated by administering the CSG polypeptide of the present invention, preferably in the secreted form, or an agonist thereof. Thus, the invention also provides a method of treatment of an individual in need of an increased level of a CSG polypeptide comprising administering to such an individual a pharmaceutical composition comprising an amount of the CSG polypeptide or an agonist thereof to increase the activity level of the CSG polypeptide in such an individual. For example, a patient with decreased levels of a CSG polypeptide may receive a daily dose 0.1–100 μg/kg of a CSG polypeptide or agonist thereof for six consecutive days. Preferably, if a CSG polypeptide is administered it is in the secreted form.

Compositions of the present invention can also be administered to treating increased levels of a CSG polypeptide. For example, antisense technology can be used to inhibit production of a CSG polypeptide of the present invention. This technology is one example of a method of decreasing levels of a polypeptide, preferably a secreted form, due to a variety of etiologies, such as cancer. A patient diagnosed with abnormally increased levels of a polypeptide can be administered intravenously antisense polynucleotides at 0.5, 1.0, 1.5, 2.0 and 3.0 mg/kg day for 21 days. This treatment is preferably repeated after a 7-day rest period if the treatment was well tolerated. Compositions comprising an antagonist of a CSG polypeptide can also be administered to decrease levels of CSG in a patient.

Gene Therapy

The CSG polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed supra. The retroviral expression construct then may be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention would be apparent to those skilled in the art upon reading the instant application.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors will include one or more promoters for expressing the polypeptide. The selection of a suitable promoter will be apparent to those skilled in the art from the teachings contained herein. However, examples of suitable promoters which may be employed include, but are not limited to, the retroviral LTR, the SV40 promoter, the human cytomegalovirus (CMV) promoter described in Miller et al., Biotechniques 7: 980–990 (1989), and eukaryotic cellular promoters such as the histone, RNA polymerase III, and beta-actin promoters. Other viral promoters which may be employed include, but are not limited to, adenovirus promoters, thymidine kinase (TK) promoters, and B19 parvovirus promoters. Additional promoters which may be used include respiratory syncytial virus (RSV) promoter, inducible promoters such as the MMT promoter, the metallothionein promoter, heat shock promoters, the albumin promoter, the ApoAI promoter, human globin promoters, viral thymidine kinase promoters such as the Herpes Simplex thymidine kinase promoter, retroviral LTRs, the beta-actin promoter, and human growth hormone promoters. The promoter also may be the native promoter which controls the gene encoding the polypeptide.

The nucleic acid sequence encoding the polypeptide of the present invention will be placed under the control of a suitable promoter.

In one embodiment, the retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAml2, and DAN cell lines as described in Miller, A., Human Gene Therapy 1: 5–14 (1990). The vector may be transduced into the packaging cells through any means known in the art. Such means include, but are not limited to, electroporation, the use of liposomes, and $CaPO_4$ precipitation. Alternatively, the retroviral plasmid vector may be encapsulated into a liposome, or coupled to a lipid, and then administered to a host. The producer cell line will generate infectious retroviral vector particles which are inclusive of the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

An exemplary method of gene therapy involves transplantation of fibroblasts which are capable of expressing a CSG polypeptide or an agonist or antagonist thereof onto a patient. Generally fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads. The cDNA encoding a CSG polypeptide of the present invention or an agonist or antagonist thereof can be amplified using PCR primers which correspond to their 5' and 3' end sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted. Amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells). Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced. The engineered fibroblasts are then transplanted onto the host, either alone or after having been grown to confluence on cytodex 3 microcarrier beads.

Alternatively, in vivo gene therapy methods can be used to treat CSG related disorders, diseases and conditions. Gene therapy methods relate to the introduction of naked nucleic acid (DNA, RNA, and antisense DNA or RNA) sequences into an animal to increase or decrease the expression of the polypeptide.

For example, a CSG polynucleotide of the present invention or a nucleic acid sequence encoding an agonist or antagonist thereto may be operatively linked to a promoter or any other genetic elements necessary for the expression of the polypeptide by the target tissue. Such gene therapy and delivery techniques and methods are known in the art, see, for example, WO 90/11092, WO 98/11779; U.S. Pat. Nos. 5,693,622, 5,705,151, and 5,580,859; Tabata H. et al. (1997) Cardiovasc. Res. 35 (3): 470–479, Chao J et al. (1997) Pharmacol. Res. 35 (6): 517–522, Wolff J. A. (1997) Neuromuscul. Disord. 7 (5): 314–318, Schwartz B. et al. (1996) Gene Ther. 3 (5): 405–411, Tsurumi Y. et al. (1996) Circulation 94 (12): 3281–3290 (incorporated herein by reference). The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, polynucleotides may also be delivered in liposome formulations (such as those taught in Felgner P. L. et al. (1995) Ann. NY Acad. Sci. 772: 126–139 and Abdallah B. et al. (1995) Biol. Cell 85 (1): 1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred. The polynucleotide construct may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 μg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

Nonhuman Transgenic Animals

The CSG polypeptides of the invention can also be expressed in nonhuman transgenic animals. Nonhuman animals of any species, including, but not limited to, mice, rats, rabbits, hamsters, guinea pigs, pigs, micro-pigs, goats, sheep, cows and non-human primates, e.g., baboons, monkeys, and chimpanzees, may be used to generate transgenic animals. Any technique known in the art may be used to introduce the transgene (I.e., polynucleotides of the invention) into animals to produce the founder lines of transgenic animals. Such techniques include, but are not limited to, pronuclear microinjection (Paterson et al., Appl. Microbiol. Biotechnol. 40: 691–698 (1994); Carver et al., Biotechnology (NY) 11: 1263–1270 (1993); Wright et al., Biotechnology (NY) 9: 830–834 (1991); and Hoppe et al., U.S. Pat. No. 4,873,191); retrovirus mediated gene transfer into germ lines (Van der Putten et al., Proc. Natl. Acad. Sci., USA 82: 6148–6152 (1985)), blastocysts or embryos; gene targeting in embryonic stem cells (Thompson et al., Cell 56: 313–321 (1989)); electroporation of cells or embryos (Lo, 1983, Mol. Cell. Biol. 3: 1803–1814 (1983)); introduction of the polynucleotides of the invention using a gene gun (see, e.g., Ulmer et al., Science 259: 1745 (1993); introducing nucleic acid constructs into embryonic pluripotent stem cells and transferring the stem cells back into the blastocyst; and sperm mediated gene transfer (Lavitrano et al., Cell 57: 717–723 (1989)). For a review of such techniques, see Gordon, "Transgenic Animals," Intl. Rev. Cytol. 115: 171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380: 64–66 (1996); Wilmut et al., Nature 385: 810813 (1997)).

The present invention provides for transgenic animals that carry the transgene in all their cells, as well as animals which carry the transgene in some, but not all their cells, i.e., mosaic or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89: 6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Science 265: 103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of CSG polypeptides of the present invention, studying conditions and/or disorders associated with aberrant expression of CSGs, and in screening for compounds effective in ameliorating such CSG associated conditions and/or disorders.

Knock-Out Animals

Endogenous gene expression can also be reduced by inactivating or "knocking out" the gene and/or its promoter using targeted homologous recombination (e.g., see Smithies et al., Nature 317: 230–234 (1985); Thomas & Capecchi, Cell 51: 503512 (1987); Thompson et al., Cell 5: 313–321 (1989); each of which is incorporated by reference herein in its entirety). For example, a mutant, non-functional CSG polynucleotide of the invention (or a completely unrelated DNA sequence) flanked by DNA homologous to the endogenous CSG polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). This approach can also be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the CSG polypeptides of the invention, or alternatively, that are genetically engineered not to express the CSG polypeptides of the invention (e.g., knockouts) are administered to a patient in vivo. Such cells may be obtained from the patient or a MHC compatible donor and can include, but are not limited to, fibroblasts, bone marrow cells, blood cells (e.g., lymphocytes), adipocytes, muscle cells, and endothelial cells. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the CSG polypeptides of the invention can be placed under the control of a strong constitutive or inducible promoter or promoter/enhancer to achieve expression, and preferably secretion, of the CSG polypeptides of the invention. The engineered cells which express and preferably secrete the CSG polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft or genetically engineered endothelial cells can be implanted as part of a lymphatic or vascular graft (see, for example, U.S. Pat. Nos. 5,399,349 and 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of CSG polypeptides of the present invention, studying conditions and/or disorders associated with aberrant CSG expression, and in screening for compounds effective in ameliorating such CSG associated conditions and/or disorders.

The following nonlimiting examples are provided to further illustrate the present invention.

EXAMPLES

The examples were carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Introduction and Background for Microarray Analysis cDNA microarrays are prepared by high-speed robotic printing of thousands of distinct cDNAs in an ordered array on glass microscope slides. They are used to measure the relative abundance of specific sequences in two complex samples (Schena et al, 1995; Shalon et al, 1996).

A brief description of the procedure for microarray use follows. mRNA is isolated from tissues of interest, either from a tumor or control (normal or normal adjacent tissue). 200–600 ng of mRNA from cancer tissue or control is reverse transcribed to incorporate the fluorescent nucleotides Cy5 (red) or Cy3 (green) respectively. The two populations of fluorescently labeled cDNA are mixed together and hybridized simultaneously to a microarray bearing approximately 10,000 cDNA elements in a 2 cm×2 cm area on a glass slide (Microarrays hybridization service: Incyte Genomics, Fremont, Calif., USA). After hybridization, the slides are scanned with a scanning laser confocal microscope.

The scanned image is used to generate the intensity and local background measurements for each spot on the array (GEMtools software, Incyte Genomics). For each spot, representing one EST, the ratio of the normalized Cy5/Cy3 intensities generates a quantitation of the gene's expression in one tissue relative to the control, in this case, the expression in cancer tissue vs. either normal or normal adjacent tissue. For example, a gene that shows a Cancer-Cy5 intensity of 3000 and a Normal-Cy3 intensity of 1000 is expressed 3-fold more in cancer tissue. Advanced analysis software is used to sort and decipher patterns of gene expression from the data (Cluster and Treeview programs, Stanford University; Eisen et al, 1998; Alizadeh et al, 2000).

References

Schena, M., D. Shalon, R. W. Davis, and P. O. Brown. 1995. Quantitative monitoring of gene expression patterns with a complementary cDNA microarray. Science 270: 467–470.

Shalon, D., S. J. Smith, and P. O. Brown. 1996. A DNA Microarray System for Anlyzing Complex DNA samples Using Two-color Fluorescent Probe Hybridization. Genome Research 6: 639–645.

Eisen, M. B., P. T. Spellman, P. O. Brown, and D. Botstein. 1998. "Cluster analysis and display of genome-wide expression patterns". PNAS 95: 14863–14868.

Alizadeh, A. A., et al, 2000. "Distinct types of diffuse large B-cell lymphoma identified by gene expression profiling."Nature, 403: 503–511.

Based on Homology Searches the Following Assignments were Made

DEX70_1 Nucleic Acid Sequence for CSG comprising Gene IDddxid 11084 (SEQ ID NO:1); Human (clone FBK III 11c) protein-tyrosine kinase (DRT)

DEX70_2 Nucleic Acid Sequence for CSG comprising Gene IDddxid 10848 (SEQ ID NO:2); Contig23 Human mRNA for glutathione peroxidase-like protein DEX70_3 Contig74 Human homeobox protein Cdxl (SEQ ID NO:3)

DEX70_4 Nucleic Acid Sequence for CSG comprising Gene IDddxid 36 (SEQ ID NO:4) Human putative secreted protein XAG DEX70_6 Contig56 Human mRNA for neutrophil gelatinase associated lipocalin (SEQ ID NO:6)

DEX70_8 Contig49 Human ATP-binding cassette protein M-ABC1, nuclear gene encoding mitochondrial protein (SEQ ID NO:8)

DEX70_9 Contig141 Human PRO2214 Mrna (SEQ ID NO:9)

DEX70_10 Nucleic Acid Sequence for CSG comprising Gene IDddxid 5250 (SEQ ID NO:10)Human Gu protein DEX70_11 Nucleic Acid Sequence for CSG comprising Gene IDddxid 10637 (SEQ ID NO:11) Human 1.6 Kb mRNA for 2–5A synthetase induced by interferon DEX70_12 Contig128 Human KRT8 mRNA for keratin 8. 0 (SEQ ID NO:12)

DEX70_14 Nucleic Acid Sequence for CSG comprising Gene IDddxid 10714 (SEQ ID NO:14) Human mRNA for Claudin-7

DEX70_17 Nucleic Acid Sequence for CSG comprising Gene ID tid331908.5 (SEQ ID NO:17) Human mRNA for p cadherin Semi-quantitative Polymerase Chain Reaction (SQ-PCR)

SQ-PCR is a method that utilizes end point PCR on serial dilutions of cDNA samples in order to determine relative expression patterns of genes of interest in multiple samples. Using random hexamer primed Reverse Transcription (RT) cDNA panels are created from total RNA samples. Gene specific primers are then used to amplify fragments using Polymerase Chain Reaction (PCR) technology from four 10×serial cDNA dilutions in duplicate. Relative expression levels of 0, 1, 10, 100 and 1000 are used to evaluate gene expression. A positive reaction in the most dilute sample indicates the highest relative expression value. This is determined by analysis of the sample reactions on a 2–4% agarose gel. The tissue samples used include 12 normal, 12 cancer and 6 pairs tissue specific cancer and matching samples.

Sequence ID #: 1 & Sequence ID #: 16 Sqcln085

Gene ID: 350214 ddxID: 11084 CloneID: 1582974T6

Semi quantitative PCR was done using the following primers:

```
Sqcln085forward:
5' GGGACAGATTGAGGAGGAAGTG 3'      (SEQ ID NO:20)

Sqcln085reverse:
5' GCTTGGGTGTCTGTGTTGGTT 3'       (SEQ ID NO:21)
```

Table 1 shows the absolute numbers which are relative levels of expression of Sqcln085 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 1

| Tissue | Normal |
|---|---|
| Breast | 1 |
| Colon | 10 |
| Endometrium | 10 |
| Kidney | 0 |
| Liver | 0 |
| Lung | 0 |
| Ovary | 10 |
| Prostate | 1 |
| Small Intestine | 1000 |
| Stomach | 10 |
| Testis | 1 |
| Uterus | 0 |

Relative levels of expression in Table 1 show that normal small intestine, stomach, and prostrate show moderate expression of Sqcln085. Low levels of expression is apparent in normal breast, colon, endometrium, kidney, lung, testis and uterus.

Table 2 shows the absolute numbers are relative levels of expression of Sqcln085 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value

TABLE 2

| Tissue | Cancer |
|---|---|
| bladder | 100 |
| breast | 1 |
| colon | 100 |
| kidney | 1 |
| liver | 1 |
| lung | 1000 |
| ovary | 100 |
| pancreas | 10 |
| prostate | 1 |
| stomach | 100 |
| testes | 10 |
| uterus | 10 |

Relative levels of expression in Table 2 show that Sqcln085 is expressed in low levels in colon, kidney, liver, lung, ovary, pancreas, prostrate, stomach and uterine carcinomas.

Table 3 shows the absolute numbers which are relative levels of expression of Sqcln085 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 3

| Sample ID | Tissue | Cancer | NAT |
|---|---|---|---|
| 9609B019 | Colon | 10 | 1 |
| 9709C074RA | Colon | 10 | 1 |
| 9705F002D | Colon | 100 | 10 |
| 9608B012 | Colon | 10 | 10 |
| 4004709A1 | Colon | 1 | 1 |
| 9707C004GB | Colon | 1 | 10 |

Relative levels of expression in Table 3 shows that Sqcln085 is expressed in moderate levels in five of the six colon cancer samples. However, high levels of expression was observed in the matching normal adjacent tissue (NAT).

Sequence ID #: 4 Sqcln088

Gene ID: 234891 ddxID: 36 CloneID: 2060915

Semi quantitative PCR was done using the following primers:

```
Sqcln088forward:
5' ACTCCTGAACACACCCTGAAGA 3'      (SEQ ID NO:22)

Sqcln088reverse:
5' ATCTCCATCTGCCTCATCAAC 3'       (SEQ ID NO:23)
```

Table 4 shows the absolute numbers which are relative levels of expression of Sqcln088 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 4

| Tissue | Normal |
|---|---|
| Breast | 0 |
| Colon | 10 |
| Endometrium | 0 |
| Kidney | 0 |
| Liver | 0 |
| Lung | 0 |
| Ovary | 0 |
| Prostate | 10 |
| Small Intestine | 1 |
| Stomach | 1 |
| Testis | 1 |
| Uterus | 0 |

Relative levels of expression in Table 4 show that normal small intestine, stomach, and testis show low expression of Sqcln088. Low levels of expression is apparent in normal colon and prostate.

Table 5 shows the absolute numbers which are relative levels of expression of Sqcln088 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 5

| Tissue | Cancer |
|---|---|
| bladder | 100 |
| breast | 100 |
| colon | 100 |
| kidney | 0 |
| liver | 0 |
| lung | 100 |
| ovary | 1 |
| pancreas | 0 |
| prostate | 10 |
| stomach | 100 |
| testes | 10 |
| uterus | 10 |

Relative levels of expression in Table 5 show that Sqcln088 is expressed in moderate levels in colon, breast, bladder, lung and stomach. Low expression levels are observed in ovary, prostrate, testis and uterine carcinomas. Table 6 shows the absolute numbers which are relative levels of expression of Sqcln088 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 6

| Sample ID | Tissue | Cancer | NAT |
|---|---|---|---|
| 9609B019 | Colon | 100 | 100 |
| 9709C074RA | Colon | 1000 | 10 |
| 9705F002D | Colon | 100 | 100 |
| 9608B012 | Colon | 10 | 100 |
| 4004709A1 | Colon | 10 | 100 |
| 9707C004GB | Colon | 100 | 100 |

Relative levels of expression in Table 6 shows that Sqcln088 is expressed in high levels in one of the six colon cancer samples. Matching expression levels were observed in three sets of colon carcinoma samples, while low levels of expression were observed in two cancer samples which also showed higher expression levels in their matching normal adjacent samples.

Sequence ID #: 7 Sqcln092

Gene ID: 234358 ddxID: 10718 CloneID: 2790863

Semi quantitative PCR was done using the following primers:

```
Sqcln092forward:
5' CACCAACAGAGCAGGCAAATGT 3'     (SEQ ID NO:24)

Sqcln092reverse:
5' TGAGCCGTGGGATGTCATAAGA 3'     (SEQ ID NO:25)
```

Table 7 shows the absolute numbers which are relative levels of expression of Sqcln092 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 7

| Tissue | Normal |
|---|---|
| Breast | 0 |
| Colon | 0 |
| Endometrium | 0 |
| Kidney | 0 |
| Liver | 0 |
| Lung | 0 |
| Ovary | 0 |
| Prostate | 0 |
| Small Intestine | 0 |
| Stomach | 0 |
| Testes | 0 |
| Uterus | 0 |

Relative levels of expression in Table 7 show that expression of Sqcln092 is absent in all normal tissue samples tested.

Table 8 shows the absolute numbers which are relative levels of expression of Sqcln092 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 8

| Tissue | Cancer |
|---|---|
| bladder | 0 |
| breast | 0 |
| colon | 1 |
| kidney | 1 |
| liver | 0 |
| lung | 0 |
| ovary | 0 |
| pancreas | 0 |
| prostate | 1 |
| stomach | 1 |
| testes | 1 |
| uterus | 1 |

Relative levels of expression in Table 8 show that Sqcln092 is expressed in low levels in colon, kidney, prostate, stomach testis and uterine carcinomas.

Table 9 shows the absolute numbers which are relative levels of expression of Sqcln092 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 9

| Sample ID | Tissue | Cancer | NAT |
|---|---|---|---|
| 9609B019 | Colon | 1 | 1 |
| 9709C074RA | Colon | 1 | 0 |
| 9705F002D | Colon | 1 | 0 |
| 9608B012 | Colon | 0 | 1 |
| 4004709A1 | Colon | 1 | 0 |
| 9707C004GB | Colon | 1 | 1 |

Relative levels of expression in Table 9 show that Sqcln092 is expressed in very low levels in five of the six colon cancer samples. However, equally low levels of expression was observed in the matching normal adjacent tissue (NAT).

Sequence ID #: 10 Sqcln094

Gene ID: 344095 ddxID: 5250 CloneID: 1702348

Semi quantitative PCR was done using the following primers:

```
Sqcln094forward:
5' GGAACACCAGGTCGTATCAAAG 3'     (SEQ ID NO:26)

Sqcln094reverse:
5' GTGCGTCCTTGATGACCACTAT 3'     (SEQ ID NO:27)
```

Table 10 shows the absolute numbers which are relative levels of expression of Sqcln094 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 10

| Tissue | Normal |
|---|---|
| Breast | 0 |
| Colon | 10 |
| Endometrium | 1 |
| Kidney | 10 |
| Liver | 1 |
| Lung | 0 |
| Ovary | 0 |
| Prostate | 10 |
| Small Intestine | 10 |
| Stomach | 10 |
| Testes | 10 |
| Uterus | 1 |

Relative levels of expression in Table 10 show low levels of expression in normal colon, endometrium, kidney, liver, prostate, small intestine, stomach, testes and uterus.

Table 11 shows the absolute numbers which are relative levels of expression of Sqcln094 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 12

| Tissue | Cancer |
|---|---|
| bladder | 1 |
| breast | 1 |
| colon | 100 |
| kidney | 100 |
| liver | 0 |
| lung | 100 |
| ovary | 10 |
| pancreas | 100 |
| prostate | 100 |
| stomach | 100 |
| testes | 100 |
| uterus | 100 |

Relative levels of expression in Table 11 show that Sqcln094 is expressed in moderate to low levels in all of the carcinoma samples except liver.

Table 12 shows the absolute numbers are relative levels of expression of Sqcln094 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 12

| Sample ID | Tissue | Cancer | NAT |
|---|---|---|---|
| 9609B019 | Colon | 100 | 1 |
| 9709C074RA | Colon | 100 | 100 |
| 9705F002D | Colon | 10 | 10 |
| 9608B012 | Colon | 10 | 100 |
| 4004709A1 | Colon | 10 | 1 |
| 9707C004GB | Colon | 10 | 100 |

Relative levels of expression in Table 12 shows that Sqcln094 is expressed in moderate to low levels in the six colon cancer samples, however, moderate to low levels of expression was also observed in the matching normal adjacent tissue (NAT).

Sequence ID #: 11 Sqcln082

Gene ID: 234866 ddxID: 10637 CloneID: 1318416 & Sequence ID# 18

Semi quantitative PCR was done using the following primers:

```
Sqcln082forward:
5' GACCCATCCCAATTCTTAAAGC 3'     (SEQ ID NO:28)

Sqcln082reverse:
5' AGGGATTTCGGACGGTCTT 3'        (SEQ ID NO:29)
```

Table 13 shows the absolute numbers which are relative levels of expression of Sqcln082 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 13

| Tissue | Normal |
|---|---|
| Breast | 1 |
| Colon | 100 |
| Endometrium | 10 |
| Kidney | 10 |
| Liver | 10 |
| Lung | 1 |
| Ovary | 100 |
| Prostate | 10 |
| Small Intestine | 100 |
| Stomach | 100 |
| Testis | 10 |
| Uterus | 100 |

Relative levels of expression in Table 13 show that normal small intestine, stomach, uterus, ovary and colon show moderate expression of Sqcln082. Low to medium levels of expression is apparent in the remaining normal tissues tested.

Table 14 shows the absolute numbers which are relative levels of expression of Sqcln082 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 14

| Tissue | Cancer |
|---|---|
| bladder | 1000 |
| breast | 1 |
| colon | 100 |
| kidney | 10 |
| liver | 1000 |
| lung | 1000 |
| ovary | 10 |
| pancreas | 100 |
| prostate | 100 |
| stomach | 1000 |
| testes | 1000 |
| uterus | 10 |

Relative levels of expression in Table 14 show that Sqcln082 is expressed in medium to high levels in bladder, colon, liver, lung, pancreas, prostate, stomach and testes carcinomas with low expression levels observed in breast.

Table 15 shows the absolute numbers which are relative levels of expression of Sqcln082 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 15

| Sample ID | Tissue | Cancer | NAT |
|---|---|---|---|
| 9609B019 | Colon | 1000 | 10 |
| 9709C074RA | Colon | 100 | 10 |
| 9705F002D | Colon | 100 | 100 |
| 9608B012 | Colon | 10 | 10 |
| 4004709A1 | Colon | 100 | 10 |
| 9707C004GB | Colon | 1000 | 100 |

Relative levels of expression in Table 15 shows that Sqcln082 is up-regulated in four of the six colon cancer samples, and equally expressed in two of the six matching samples.

Sequence ID #: 12 Sqcln083 also known as keratin 8.0 protein

Gene ID: 263164 ddxID: 15607 CloneID: 1866774

Semi quantitative PCR was done using the following primers:

```
Sqcln083forward:
5' CCAGGAGAAGGAGCAGATCAAG 3'     (SEQ ID NO:30)

Sqcln083reverse:
5' CGGTTGGCAATATCCTCGTACT 3'     (SEQ ID NO:31)
```

Table 16 shows the absolute numbers which are relative levels of expression of Sqcln083 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 16

| Tissue | Normal |
|---|---|
| Breast | 0 |
| Colon | 100 |
| Endometrium | 1 |
| Kidney | 10 |
| Liver | 10 |
| Lung | 1 |
| Ovary | 1 |
| Prostate | 100 |
| Small Intestine | 10 |
| Stomach | 10 |
| Testis | 1 |
| Uterus | 1 |

Relative levels of expression in Table 16 show that normal colon and prostate express moderate levels of Sqcln083. Low levels of expression is apparent in the remaining normal tissues.

Table 17 shows the absolute numbers which are relative levels of expression of Sqcln083 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 17

| Tissue | Cancer |
|---|---|
| bladder | 1000 |
| breast | 10 |
| colon | 1000 |
| kidney | 100 |
| liver | 10 |
| lung | 100 |
| ovary | 100 |
| pancreas | 1000 |
| prostate | 100 |
| stomach | 1000 |
| testes | 100 |
| uterus | 100 |

Relative levels of expression in Table 17 show that Sqcln083 is expressed in high levels in colon, bladder, pancreas, and stomach. Expression is of a moderate to low expression in breast, kidney, liver, lung, ovary, prostate, testes and uterine carcinomas.

Table 18 shows the absolute numbers which are relative levels of expression of Sqcln083 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 18

| Sample ID | Tissue | Cancer | NAT |
|---|---|---|---|
| 9609B019 | Colon | 1000 | 100 |
| 9709C074RA | Colon | 1000 | 100 |
| 9705F002D | Colon | 10 | 1000 |
| 9608B012 | Colon | 100 | 100 |
| 4004709A1 | Colon | 10 | 1 |
| 9707C004GB | Colon | 10 | 10 |

Relative levels of expression in Table 18 shows that Sqcln083 is up-regulated in three of the six colon cancer samples, equally expressed in two of the matching samples and down regulated in one of the six matching samples.

Sequence ID #: 13 Sqcln084

Gene ID: 337679 ddxID: 5642 CloneID: 1939239

Semi quantitative PCR was done using the following primers:

```
Sqcln084forward:
5' ACGCTGAAGTCCCTGTTTTGTT 3'     (SEQ ID NO:32)

Sqcln084reverse:
5' TTCGGCTGGCATTTGACTAAG 3'      (SEQ ID NO:33)
```

Table 19 shows the absolute numbers which are relative levels of expression of Sqcln084 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 19

| Tissue | Normal |
|---|---|
| Breast | 0 |
| Colon | 1 |
| Endometrium | 0 |
| Kidney | 0 |
| Liver | 0 |
| Lung | 0 |
| Ovary | 0 |
| Prostate | 0 |
| Small Intestine | 0 |
| Stomach | 0 |
| Testis | 0 |
| Uterus | 0 |

Relative levels of expression in Table 19 show that only normal colon exhibited low levels of gene expression.

Table 20 shows the absolute numbers which are relative levels of expression of Sqcln084 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 20

| Tissue | Cancer |
|---|---|
| bladder | 0 |
| breast | 1 |
| colon | 1 |
| kidney | 0 |
| liver | 0 |
| lung | 1 |
| ovary | 0 |
| pancreas | 0 |
| prostate | 1 |
| stomach | 1 |
| testes | 0 |
| uterus | 0 |

Relative levels of expression in Table 20 show that Sqcln084 is expressed in low levels in colon, breast, lung, prostate, and stomach carcinomas.

Table 21 shows the absolute numbers which are relative levels of expression of Sqcln084 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 21

| Sample ID | Tissue | Cancer | NAT |
|---|---|---|---|
| 9609B019 | Colon | 1 | 1 |
| 9709C074RA | Colon | 1 | 0 |
| 9705F002D | Colon | 1 | 1 |
| 9608B012 | Colon | 1 | 1 |
| 4004709A1 | Colon | 1 | 0 |
| 9707C004GB | Colon | 0 | 1 |

Relative levels of expression in Table 21 shows that Sqcln084 is expressed in low levels in five of the six colon cancer samples. However, low levels of expression was observed in the matching normal adjacent tissue (NAT).

Sequence ID #: 14 Sqcln099

Gene ID: 255990 ddxID: 10714 CloneID: 1696345

Semi quantitative PCR was done using the following primers:

```
Sqcln099forward:
5' GCTCCTATGCGGGTGACAAC 3'       (SEQ ID NO:34)

Sqcln099reverse:
5' GTCACACATACTCCTTGGAAGA 3'     (SEQ ID NO:35)
```

Table 22 shows the absolute numbers which are relative levels of expression of Sqcln099 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 22

| Tissue | Normal |
| --- | --- |
| Breast | 0 |
| Colon | 1 |
| Endometrium | 0 |
| Kidney | 0 |
| Liver | 0 |
| Lung | 0 |
| Ovary | 0 |
| Prostate | 0 |
| Small Intestine | 0 |
| Stomach | 0 |
| Testis | 0 |
| Uterus | 0 |

Relative levels of expression in Table 22 showed low levels of Sqcln099 expression in normal colon only.

Table 23 shows the absolute numbers which are relative levels of expression of Sqcln099 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 23

| Tissue | Cancer |
| --- | --- |
| bladder | 1 |
| breast | 1 |
| colon | 10 |
| kidney | 10 |
| liver | 0 |
| lung | 1 |
| ovary | 1 |
| pancreas | 0 |
| prostate | 10 |
| stomach | 1000 |
| testes | 100 |
| uterus | 10 |

Relative levels of expression in Table 23 show that Sqcln099 is expressed at high levels in stomach cancer tissue, and moderate to low levels in testes, uterus, prostate, kidney, and colon. Very low expression is observed in bladder, breast, ovary and lung carcinomas.

Table 24 shows the absolute numbers which are relative levels of expression of Sqcln099 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 24

| Sample ID | Tissue | Cancer | NAT |
| --- | --- | --- | --- |
| 9609B019 | Colon | 10 | 1 |
| 9709C074RA | Colon | 100 | 0 |
| 9705F002D | Colon | 10 | 10 |
| 9608B012 | Colon | 10 | 10 |
| 4004709A1 | Colon | 10 | 10 |
| 9707C004GB | Colon | 100 | 10 |

Relative levels of expression in Table 24 shows that Sqcln099 is up-regulated in three of the six colon cancer samples, and equally expressed in three of the colon matched samples.

Sequence ID #: 17 Sqcln097
Gene ID: 331908 ddxID: 64424 TID: 331908.5

Semi quantitative PCR was done using the following primers:

```
Sqcln097forward:
5' ACAGCCACAGATGAGGATGAT 3'      (SEQ ID NO:36)

Sqcln097reverse:
5' CACTGGAGATGACGCTGATG 3'       (SEQ ID NO:37)
```

Table 25 shows the absolute numbers which are relative levels of expression of Sqcln097 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 25

| Tissue | Normal |
| --- | --- |
| Breast | 10 |
| Colon | 0 |
| Endometrium | 10 |
| Kidney | 10 |
| Liver | 1 |
| Lung | 1 |
| Ovary | 100 |
| Prostate | 10 |
| Small Intestine | 0 |
| Stomach | 0 |
| Testis | 100 |
| Uterus | 10 |

Relative levels of expression in Table 25 show that normal ovary and testis show moderate expression of Sqcln097. Low levels of expression is apparent in normal breast, endometrium, kidney, liver, lung, prostate and uterus.

Table 26 shows the absolute numbers which are relative levels of expression of Sqcln097 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 26

| Tissue | Cancer |
| --- | --- |
| bladder | 10 |
| breast | 10 |
| colon | 10 |
| kidney | 1 |
| liver | 0 |
| lung | 1000 |
| ovary | 10 |
| pancreas | 10 |
| prostate | 10 |
| stomach | 100 |
| testes | 100 |
| uterus | 100 |

Relative levels of expression in Table 26 show that Sqcln097 is expressed to a high level in lung carcinoma, and moderate to low levels in bladder, breast, colon, kidney, ovary, pancreas, prostrate, stomach, testes and uterine carcinomas.

Table 27 shows the absolute numbers which are relative levels of expression of Sqcln097 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 27

| Sample ID | Tissue | Cancer | NAT |
|---|---|---|---|
| 9609B019 | Colon | 100 | 1 |
| 9709C074RA | Colon | 100 | 0 |
| 9705F002D | Colon | 100 | 0 |
| 9608B012 | Colon | 100 | 1 |
| 4004709A1 | Colon | 100 | 1 |
| 9707C004GB | Colon | 100 | 1 |

Relative levels of expression in Table 27 show that Sqcln097 is up-regulated in all of the six colon cancer matched samples.

Sequence ID #: 19 Sqcln081

Gene ID: 337151 ddxID: 65291 TID: 337151.3

Semi quantitative PCR was done using the following primers:

```
Sqcln081forward:
5' GCCCTTGTGCCTAGTTAAGAGC 3'      (SEQ ID NO:38)

Sqcln081reverse:
5' AGGGGCACAACTCTCTTCAAAC 3'      (SEQ ID NO:39)
```

Table 28 shows the absolute numbers which are relative levels of expression of Sqcln181 in 12 normal samples from 12 different tissues. These RNA samples are individual samples or are commercially available pools, originated by pooling samples of a particular tissue from different individuals. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 28

| Tissue | Normal |
|---|---|
| Breast | 0 |
| Colon | 10 |
| Endometrium | 10 |
| Kidney | 10 |
| Liver | 10 |
| Lung | 0 |
| Ovary | 10 |
| Prostate | 10 |
| Small Intestine | 10 |
| Stomach | 10 |
| Testis | 10 |
| Uterus | 1 |

Relative levels of expression in Table 28 show that except for normal lung which did not exhibit expression of Sqcln181, low levels of Sqcln181 expression is observed in the remaining normal tissues.

Table 29 shows the absolute numbers which are relative levels of expression of Sqcln081 in 12 cancer samples from 12 different tissues. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 29

| Tissue | Cancer |
|---|---|
| bladder | 1 |
| breast | 1 |
| colon | 1 |
| kidney | 10 |
| liver | 1 |
| lung | 10 |
| ovary | 10 |
| pancreas | 1 |
| prostate | 1 |
| stomach | 1 |
| testes | 10 |
| uterus | 1 |

Relative levels of expression in Table 29 show that Sqcln081 is expressed in low levels in all the carcinomas tested here.

Table 30 shows the absolute numbers which are relative levels of expression of Sqcln081 in 6 colon cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10×serial cDNA dilutions in duplicate. Relative expression levels of 0, 1, 10, 100 and 1000 are used to evaluate gene expression. A positive reaction in the most dilute sample indicates the highest relative expression value.

TABLE 30

| Sample ID | Tissue | Cancer | NAT |
|---|---|---|---|
| 9609B019 | Colon | 10 | 1 |
| 9709C074RA | Colon | 1 | 1 |
| 9705F002D | Colon | 1 | 1 |
| 9608B012 | Colon | 10 | 100 |
| 4004709A1 | Colon | 1 | 1 |
| 9707C004GB | Colon | 1 | 10 |

Relative levels of expression in Table 30 show that Sqcln081 is upregulated in cancer in one of the six matched sets while is equally present or downregulated in 5 of the six colon cancer matching samples.

What is claimed is:

1. An isolated polynucleotide comprising:

(a) SEQ ID NO:7; or (b) a polynucleotide with 95% identity to SEQ ID NO:7 and which is capable of hybridizing under stringent conditions to the antisense of SEQ ID NO: 7 and which is overexpressed in colon cancer tissue.

* * * * *

SEQUENCE LISTING

<160> NUMBER OF SEQ ID NOS: 39

<210> SEQ ID NO 1
<211> LENGTH: 4698
<212> TYPE: DNA
<213> ORGANISM: Homo sapiens
<220> FEATURE:
<221> NAME/KEY: unsure
<222> LOCATION: (3921)

<400> SEQUENCE: 1

```
taacacagtt gtgaaaagag atggatgtgg gttccagtcc tagccctgcc tgtgtgcact     60

tatgcagaaa cgctaatgga ctccactaca gcgactgctg agctgggctg gatggtgcat    120

cctccatcag ggtgggaaga ggtgagtggc tacgatgaga acatgaacac gatccgcacg    180

taccaggtgt gcaacgtgtt tgagtcaagc cagaacaact ggctacggac caagtttatc    240

cggcgccgtg gcgcccaccg catccacgtg gagatgaagt tttcggtgcg tgactgcagc    300

agcatcccca gcgtgcctgg ctcctgcaag gagaccttca acctctatta ctatgaggct    360

gactttgact cggccaccaa gaccttcccc aactggatgg agaatccatg ggtgaaggtg    420

gataccattg cagccgacga gagcttctcc caggtggacc tgggtggccg cgtcatgaaa    480

atcaacaccg aggtgcggag cttcggacct gtgtcccgca gcggcttcta cctggccttc    540

caggactatg gcggctgcat gtccctcatc ggccgtgcgt gtcttctacc gcaagtgccc    600

ccgcatcatc cagaatggcg ccatcttcca ggaaaccctg tcgggggctg agagcacatc    660

gctggtggct gcccggggca gctgcatcgc caatgcggaa gaggtggatg tacccatcaa    720

gctctactgt aacggggacg gcgagtggct ggtgcccatc gggcgctgca tgtgcaaagc    780

aggcttcgag gccgttgaga atggcaccgt ctgccgaggt tgtccatctg ggactttcaa    840

ggccaaccaa ggggatgagg cctgtaccca ctgtcccatc aacagccgga ccacttctga    900

aggggccacc aactgtgtct gccgcaatgg ctactacaga gcagacctgg accccctgga    960

catgccctgc acaaccatcc cctccgcgcc ccaggctgtg atttccagtg tcaatgagac   1020

ctccctcatg ctggagtgga cccctccccg cgactccgga ggccgagagg acctcgtcta   1080

caacatcatc tgcaagagct gtggctcggg ccggggtgcc tgcacccgct gcggggacaa   1140

tgtacagtac gcaccacgcc agctaggcct gaccgagcca cgcatttaca tcagtgacct   1200

gctggcccac acccagtaca ccttcgagat ccaggctgtg aacggcgtta ctgaccagag   1260

ccccttctcg cctcagttcg cctctgtgaa catcaccacc aaccaggcag ctccatcggc   1320

agtgtccatc atgcatcagg tgagccgcac cgtggacagc attaccctgt cgtggtccca   1380

gccagaccag cccaatggcg tgatcctgga ctatgagctg cagtactatg agaaggagct   1440

cagtgagtac aacgccacag ccataaaaag ccccaccaac acggtcaccg tgcagggcct   1500

caaagccggc gccatctatg tcttccaggt gcgggcacgc accgtggcag gctacgggcg   1560

ctacagcggc aagatgtact tccagaccat gacagaagcc gagtaccaga caagcatcca   1620

ggagaagttg ccactcatca tcggctcctc ggccgctggc ctggtcttcc tcattgctgt   1680

ggttgtcatc gccatcgtgt gtaacagaag acgggggttt gagcgtgctg actcggagta   1740

cacggacaag ctgcaacact acaccagtgg ccacatgacc ccaggcatga agatctacat   1800

cgatcctttc acctacgagg accccaacga ggcagtgcgg gagtttgcca aggaaattga   1860

catctcctgt gtcaaaattg agcaggtgat cggagcaggg gagtttggcg aggtctgcag   1920
```

-continued

```
tggccacctg aagctgccag gcaagagaga gatctttgtg gccatcaaga cgctcaagtc   1980
gggctacacg gagaagcagc gccgggactt cctgagcgaa gcctccatca tgggccagtt   2040
cgaccatccc aacgtcatcc acctggaggg tgtcgtgacc aagagcacac ctgtgatgat   2100
catcaccgag ttcatggaga atggctccct ggactccttt ctccggcaaa acgatgggca   2160
gttcacagtc atccagctgg tgggcatgct tcggggcatc gcagctggca tgaagtacct   2220
ggcagacatg aactatgttc accgtgacct ggctgcccgc aacatcctcg tcaacagcaa   2280
cctggtctgc aaggtgtcgg actttgggct ctcacgcttt ctagaggacg atacctcaga   2340
ccccacctac accagtgccc tgggcggaaa gatccccatc cgctggacag ccccggaagc   2400
catccagtac cggaagttca cctcggccag tgatgtgtgg agctacggca ttgtcatgtg   2460
ggaggtgatg tcctatgggg agcggcccta ctgggacatg accaaccagg atgtaatcaa   2520
tgccattgag caggactatc ggctgccacc gcccatggac tgcccgagcg ccctgcacca   2580
actcatgctg gactgttggc agaaggaccg caaccaccgg cccaagttcg gccaaattgt   2640
caacacgcta gacaagatga tccgcaatcc caacagcctc aaagccatgg cgcccctctc   2700
ctctggcatc aacctgccgc tgctggaccg cacgatcccc gactacacca gctttaacac   2760
ggtggacgag tggctggagg ccatcaagat ggggcagtac aaggagagct tcgccaatgc   2820
cggcttcacc tcctttgacg tcgtgtctca gatgatgatg gaggacattc tccgggttgg   2880
ggtcactttg gctggccacc agaaaaaaat cctgaacagt atccaggtga tgcgggcgca   2940
gatgaaccag attcagtctg tggaggtttg acattcacct gcctcggctc acctcttcct   3000
ccaagccccg cccctctgc cccacgtgcc ggccctcctg gtgctctatc cactgcaggg   3060
ccagccactc gccaggaggc cacgggccac gggaagaacc aagcggtgcc agccacgaga   3120
cgtcaccaag aaaacatgca actcaaacga cggaaaaaaa aagggaatgg gaaaaaagaa   3180
aacagatcct gggagggggc gggaaataca aggaatattt tttaaagagg attctcataa   3240
ggaaagcaat gactgttctt gcgggggata aaaaagggct tgggagattc atgcgatgtg   3300
tccaatcgga gacaaaagca gtttctctcc aactccctct gggaaggtga cctggccaga   3360
gccaagaaac actttcagaa aaacaaatgt gaaggggaga gacaggggcc gcccttggct   3420
cctgtccctg ctgctcctct aggcctcact caacaaccaa gcgcctggag gacgggacag   3480
atggacagac agccaccctg agaacccctc tgggaaaatc tattcctgcc accactgggc   3540
aaacagaaga atttttctgt ctttggagag tattttagaa actccaatga aagacactgt   3600
ttctcctgtt ggctcacagg gctgaaaggg gcttttgtcc tcctgggtca gggagaacgc   3660
ggggacccca gaaaggtcag ccttcctgag gatgggcaac cccaggtct gcagctccag   3720
gtacatatca cgcgcacagc ctggcagcct ggccctcctg gtgcccactc ccgccagccc   3780
ctgcctcgag gactgatact gcagtgactg ccgtcagctc cgactgccgc tgagaagggt   3840
tgatcctgca tctgggtttg tttacagcaa ttcctggact cgggggtatt ttggtcacag   3900
ggtggttttg gtttaggggg nttgtttgtt gggttgtttt ttgttttttg gttttttta   3960
atgacaatga agtgacactt tgacatttcc taccttttga ggacttgatc cttctccagg   4020
aagaaggtgc tttctgctta ctgacttagg caatacacca agggcgagat tttatatgca   4080
catttctgga ttttttata cggttttcat tgacactctt ccctcctccc acctgccacc   4140
aggcctcacc aaagcccact gccatggggc catctgggcc attcagagac tggagtgaga   4200
tttgggtgtg gaggggagg cgccaaggtg gaggagcttc ccactccagg actgttgatg   4260
aaagggacag attgaggagg aagtgggctc tgaggctgca gggctggaag tccttgccca   4320
```

-continued

```
cttcccactc tcctgcccca atctatctag tacttcccag gcaaataggc ccctttgagg   4380

ctcctgagtg ccctcagatg gtcaaaaccc agttttccct ctgggagcct aaaccaggct   4440

gcatcggagg ccaggacccg gatcattcac tgtgataccc tgccctccag agggtgcgct   4500

cagagacacg ggcaagcatg cctcttccct tccctggaga gaaagtgtgt gatttctctc   4560

ccacctcctt ccccccacca gacctttgct gggcctaaag gtcttggcca tggggacgcc   4620

ctcagtctag ggatctggcc acagactccc tcctgtgaac caacacagac acccaagcag   4680

agcaatcagt tagtgaat                                                 4698
```

<210> SEQ ID NO 2
<211> LENGTH: 1496
<212> TYPE: DNA
<213> ORGANISM: Homo sapiens

<400> SEQUENCE: 2

```
acgcggctga ctacgctcaa agctccattg ttagatcctt tctgtcctcc ttcctggctc     60

ctccttcctc cccacccctc taataggctc ataagtgggc tcaggcctct ctgcggggct    120

cactctgcgc ttcaccatgg ctttcattgc caagtccttc tatgacctca gtgccatcag    180

cctggatggg gagaaggtag atttcaatac gttccggggc cagggccgtg cctgattgag    240

aatgtggctt cgctctgagg cacaaccacc cgggacttca cccagctcaa cgagctgcaa    300

tgccgctttc ccaggcgcct ggtggtcctt ggcttccctt gcaaccaatt tggacatcag    360

gagaactgtc agaatgagga gatcctgaac agtctcaagt atgtccgtcc tgggggtgga    420

taccagccca ccttcaccct tgtccaaaaa tgtgaggtga atgggcagaa cgagcatcct    480

gtcttcgcct acctgaagga caagctcccc tacccttatg atgacccatt ttccctcatg    540

accgatccca agctcatcat ttggagccct gtgcgccgct cagatgtggc ctggaacttt    600

gagaagttcc tcatagggcc ggagggagag cccttccgac gctacagccg caccttccca    660

accatcaaca ttgagcctga catcaagcgc ctccttaaag ttgccatata gatgtgaact    720

gctcaacaca cagatctcct actccatcca gtcctgagga gccttaggat gcagcatgcc    780

ttcaggagac actgctggac ctcagcattc ccttgatatc agtccccttc actgcagagc    840

cttgcctttc ccctctgcct gtttcctttt cctctcccaa ccctctggtt ggtgattcaa    900

cttgggctcc aagacttggg taagctctgg gccttcacag aatgatggca ccttcctaaa    960

ccctcatggg tggtgtctga gaggcgtgaa gggcctggag ccactctgct agaagagacc   1020

aataaagggc agggtggtgg gaaccaccaa acaacaccac caaacacaac acaacaataa   1080

aagaaaaaca caacaaaaca caaaaccaac aacaaaaaac aaacaagaac aaccccacgg   1140

cggggaccac atcattctag gagcggcggg cgcaaaacaa aggggaagtc caaacagaac   1200

agcgaccacg cagggcacaa caaagaaagg atcatcccca cccaccacca cacacctttt   1260

gttggccacc acaccacaag gaggggacaa ccacacaccg cgggccagcc cccccccaa    1320

aataggaggg cggcggagca caaaacataa cgcacagaca aacaccacca gaggtgataa   1380

ccacgccgga aaacaaacgt ctcacgcgcc ccagagacga tgcccagacc agccgagcat   1440

cgaacaccac ccacgcagcg cagaacagcc cgaccagcgc gggcgacaga acaacc       1496
```

<210> SEQ ID NO 3
<211> LENGTH: 1856
<212> TYPE: DNA
<213> ORGANISM: Homo sapiens -continued

<400> SEQUENCE: 3

```
gtttaggtga gcggttgctc gtcgtcgggg cggccggcag cggcggctcc agggcccagc      60
atgcgcgggg gaccccgcgg ccaccatgta tgtgggctat gtgctggaca aggattcgcc     120
cgtgtacccc ggcccagcca ggccagccag cctcggcctg ggcccggcaa actacggccc     180
cccggccccg cccccggcgc ccccgcagta ccccgacttc tccagctact ctcacgtgga     240
gccggccccc gcgcccccga cggcctgggg ggcgcccttc cctgcgccca aggacgactg     300
ggccgccgcc tacggcccgg gccccgcggc ccctgccgcc agcccagctt cgctggcatt     360
cgggccccct ccagacttta gcccggtgcc ggcgccccct gggcccggcc cgggcctcct     420
ggcgcagccc ctcgggggcc cgggcacacc gtcctcgccc ggagcgcaga ggccgacgcc     480
ctacgagtgg atgcggcgca gcgtggcggc cggaggcggc ggtggcagcg gtaagactcg     540
gaccaaggac aagtaccgcg tggtctacac cgaccaccaa cgcctggagc tggagaagga     600
gtttcattac agccgttaca tcacaatccg gcggaaatca gagctggctg ccaatctggg     660
gctcactgaa cggcaggtga agatctggtt ccaaaaccgg cgggcaaagg agcgcaaagt     720
gaacaagaag aaacagcagc agcaacagcc cccacagccg ccgatggccc acgacatcac     780
ggccacccca gccgggccat ccctgggggg cctgtgtccc agcaacacca gcctcctggc     840
cacctcctct ccaatgcctg tgaaagagga gtttctgcca tagccccatg cccagcctgt     900
gcgccggggg acctggggac tcgggtgctg ggagtgtggc tcctgtgggc ccaggaggtc     960
tggtccgagt ctcagccctg accttctggg acatggtgga cagtcaccta tccaccctct    1020
gcatcccctt ggcccatctg tgcagtaagc ctgttggata aagaccttcc agctcctgtg    1080
ttctagacct ctggggata agggagtcca gggtggatga tctcaatctc ccgtgggcat    1140
ctcaagcccc aaatggttgg gggaggggcc tagacaaggc tccaggcccc acctcctcct    1200
ccatacgttc agaggtgcag ctggaggctg ctgtggggac cacactgatc ctggagaaaa    1260
gggatggagc tgaaaaagat ggaatgcttg cagagcatga cctgaggagg gaggaacgtg    1320
gtcaactcac acctgcctct tcctgcagcc tcacctctac ctgcccccat cataagggca    1380
ctgagccctt cccaggctgg atactaagca caaagcccat agcactgggc tctgatggct    1440
gctccactgg gttacagaat cacagccctc atgatcattc tcagtgaggg ctctggattg    1500
agagggaggc cctgggagga gagaaggggg cagagtcttc cctaccaggt ttctacaccc    1560
ccgccaggct gcccatcagg gcccagggag cccccagagg actttattcg gaccaagcag    1620
agctcacagc tggacaggtg ttgtatatag agtggaatct cttggatgca gcttcaagaa    1680
taaatttttc ttctcttttc aaaaatgtat aaaaatcatt atacatagca ttaaagaaac    1740
atttttgaga agtacaaatc atcctcacct tccccagcaa ttgtgtattc ctttcccgtt    1800
tgtttaggcc cagaagaagg tcacctttaa aatacatttg aaagatcaaa acagaa        1856
```

<210> SEQ ID NO 4
<211> LENGTH: 1860
<212> TYPE: DNA
<213> ORGANISM: Homo sapiens

<400> SEQUENCE: 4

```
ggcagatggc agggtccttt gcaggagagg cagcggcgaa agctgccctt aggaggcagc      60
gaggaggtga aaccagagag caacaagtaa atgcagcact agtgggtggg attgaggtgt     120
gccctggtgc ataaatagag actcagctgt gctggcacac tcagaagctt ggaccgcatc     180
ctagccgccg actcacacaa ggcaggtggg tgaggaaatc cagagttgcc atggagaaaa     240
```

-continued

```
ttccagtgtc agcattcttg ctccttgtgg ccctctccta cactctggcc agagatacca     300

cagtcaaacc tggagccaaa aaggacacaa aggactctcg acccaaactg ccccagaccc     360

tctccagagg ttggggtgac caactcatct ggactcagac atatgaagaa gctctatata     420

aatccaagac aagcaacaaa cccttgatga ttattcatca cttggatgag tgcccacaca     480

gtcaagcttt aaagaaagtg tttgctgaaa ataaagaaat ccagaaattg gcagagcagt     540

ttgtcctcct caatctggtt tatgaaacaa ctgacaaaca cctttctcct gatggccagt     600

atgtccccag gattatgttt gttgacccat ctctgacagt tagagccgat atcactggaa     660

gatattcaaa tcgtctctat gcttacgaac ctgcagatac agctctgttg cttgacaaca     720

tgaagaaagc tctcaagttg ctgaagactg aattgtaaag aaaaaaaatc tccaagccct     780

tctgtctgtc aggccttgag acttgaaacc agaagaagtg tgagaagact ggctagtgtg     840

gaagcatagt gaacacactg attaggttat ggtttaatgt tacaacaact attttttaag     900

aaaaacaagt tttagaaatt tggtttcaag tgtacatgtg tgaaaacaat attgtatact     960

accatagtga gccatgattt tctaaaaaaa aaaataaatg ttttgggggt gttctgtttt    1020

ctccaacttg gtctttcaca gtggttcgtt taccaaatag gattaaacac acacaaaatg    1080

ctcaaggaag ggacaagaca aaaccaaaac tagttcaaat gatgaagacc aaagaccaag    1140

ttatcatctc accacaccac aggttctcac tagatgactg taagtagaca cgagcttaat    1200

caacagaagt atcaagccat gtgctttagc ataaaagaat atttagaaaa acatcccaag    1260

aaaatcacat cactacctag agtcaactct ggccaggaac tctaaggtac acactttcat    1320

ttagtaatta aattttagtc agattttgcc caacctaatg ctctcaggga aagcctctgg    1380

caagtagctt tctccttcag aggtctaatt tagtagaaag gtcatccaaa gaacatctgc    1440

actcctgaac acaccctgaa gaaatcctgg gaattgacct tgtaatcgat ttgtctgtca    1500

aggtcctaaa gtactggagt gaaataaatt cagccaacat gtgactaatt ggaagaagag    1560

caaagggtgg tgacgtgttg atgaggcaga tggagatcag aggttactag ggtttaggaa    1620

acgtgaaagg ctgtggcatc agggtagggg agcattctgc ctaacagaaa ttagaattgt    1680

gtgttaatgt cttcactcta tacttaatct cacattcatt aatatatgga attcctctac    1740

tgcccagccc ctcctgattt ctttggcccc tggactatgg tgctgtatat aatgctttgc    1800

agtatctgtt gcttgtcttg attaactttt ttggataaaa ccttttttga acagaaaaaa    1860
```

<210> SEQ ID NO 5
<211> LENGTH: 888
<212> TYPE: DNA
<213> ORGANISM: Homo sapiens

<400> SEQUENCE: 5

```
gtgcctggtg cataaataga gactcagctg tgctggcaca ctcagaagct tggaccgcat      60

cctagccgcc gactcacaca aggcagagtt gccatggaga aaattccagt gtcagcattc     120

ttgctccttg tggccctctc ctacactctg ggccagagat accacagtca aacctggagc     180

caaaaaggac acaaaggact ctcgacccaa actgccccag accctctcca gaggttgggg     240

tgaccaactc atctggactc agacatatga agaagctcta tataaatcca agacaagcaa     300

caaacccttg atgattattc atcacttgga tgagtgccca cacagtcaag ctttaaagaa     360

agtgtttgct gaaaataaag aaatccagaa attggcagag cagtttgtcc tcctcaatct     420

ggtttatgaa acaactgaca aacacctttc tcctgatggc cagtatgtcc ccaggattat     480
```

-continued

```
gtttgttgac ccatctctga cagttagagc cgatatcact ggaagatatt caaaccgtct    540

ctatgcttac gaacctgcag atacagctct gttgcttgac aacatgaaga aagctctcaa    600

gttgctgaag actgaattgt aaagaaaaaa aatctccaag cccttctgtc tgtcaggcct    660

tgagacttga aaccagaaga agtgtgagaa gactggctag tgtggaagca tagtgaacac    720

actgattagg ttatggttta atgttacaac aactattttt taagaaaaac aagttttaga    780

aatttggttt caagtgtaca tgtgtgaaaa caatattgta tactaccata gtgagccatg    840

attttctaaa aaaaaaaata aatgttttgg gggtgttctg ttttctcc                 888
```

<210> SEQ ID NO 6
<211> LENGTH: 850
<212> TYPE: DNA
<213> ORGANISM: Homo sapiens

<400> SEQUENCE: 6

```
tctagatcgc gagcggccgg tgcgtctaga acctcttcca cccctgccag gcccagcagc     60

caccacagcg cctgcttcct cggccctgaa atcatgcccc taggtctcct gtggctgggc    120

ctagccctgt tgggggctct gcatgcccag gcccaggact ccacctcaga cctgatccca    180

gccccacctc tgagcaaggt ccctctgcag cagaacttcc aggacaacca attccagggg    240

aagtggtatg tggtaggcct ggcagggaat gcaattctca gagaagacaa agacccgcaa    300

aagatgtatg ccaccatcta tgagctgaaa gaagacaaga gctacaatgt cacctccgtc    360

ctgtttagga aaaagaagtg tgactactgg atcaggactt ttgttccagg ttgccagccc    420

ggcgagttca cgctgggcaa cattaagagt taccctggat taacgagtta cctcgtccga    480

gtggtgagca ccaactacaa ccagcatgct atggtgttct tcaagaaagt ttctcaaaac    540

agggagtact tcaagatcac cctctacggg agaaccaagg agctgacttc ggaactaaag    600

gagaacttca tccgcttctc caaatctttg ggcctccctg aaaaccacat cgttttccct    660

gtcccaatcg accagtgtat cgacggctga gtgcacaggt gccgccagct gccgcaccag    720

cccgaacacc attgagggag ctgggagacc ctccccacag tgccacccat gcagttgctc    780

cccaggccac cccgctgatg gagccccccc ttgtttgcta aataaacatg tgccctcagg    840

aaaaaaaaaa                                                           850
```

<210> SEQ ID NO 7
<211> LENGTH: 4142
<212> TYPE: DNA
<213> ORGANISM: Homo sapiens

<400> SEQUENCE: 7

```
cggccgccgg cgaggaatgg cggtatttgt gagaggagtc ggcgtttgaa gaggtggaac     60

tcctagggct tttttgagag tgctgattta gaagaataca aatcatggct gaaaatagtg    120

tattaacatc cactactggg aggactagct tggcagactc ttccattttt gattctaaag    180

ttactgagat ttccaaggaa aacttactta ttggatctac ttcatatgta gaagaagaga    240

tgcctcagat tgaaacaaga gtgatattgg ttcaagaagc tggaaaacaa gaagaactta    300

taaaagcctt aaaggacatt aaagtgggct ttgtaaagat ggagtcagtg gaagaatttg    360

aaggtttgga ttctccggaa tttgaaaatg tatttgtagt cacggacttt caggattctg    420

tctttaatga cctctacaag gctgattgta gagttattgg accaccagtt gtattaaatt    480

gttcacaaaa aggagagcct ttgccatttt catgtcgccc gttgtattgt acaagtatga    540

tgaatctagt actatgcttt actggattta ggaaaaaaga agaactagtc aggttggtga    600
```

-continued

```
cattggtcca tcacatgggt ggagttattc gaaaagactt taattcaaaa gttacacatt    660
tggtggcaaa ttgtacacaa ggagaaaaat tcagggttgc tgtgagtcta ggtactccaa    720
ttatgaagcc agaatggatt tataaagctt gggaaaggcg gaatgaacag gatttctatg    780
cagcagttga tgactttaga aatgaattta aagttcctcc atttcaagat tgtattttaa    840
gtttcctggg attttcagat gaagagaaaa ccaatatgga agaaatgact gaaatgcaag    900
gaggtaaata tttaccgctt ggagatgaaa gatgcactca ccttgtagtt gaagagaata    960
tagtaaaaga tcttcccttt gaaccttcaa agaaacttta tgttgtcaag caagagtggt   1020
tctggggaag cattcaaatg gatgcccgag ctggagaaac tatgtattta tatgaaaagg   1080
caaatactcc tgagctcaag aaatcagtgt caatgctttc tctaaatacc cctaacagca   1140
atcgcaaacg acgtcgttta aaagaaacac ttgctcagct ttcaagagag acagacgtgt   1200
caccatttcc accccgtaag cgcccatcag ctgagcattc cctttccata gggtcactcc   1260
tagatatctc caacacacca gagtctagca ttaactatgg agacacccca aagtcttgta   1320
ctaagtcttc taaaagctcc actccagttc cttcaaagca gtcagcaagg tggcaagttg   1380
caaaagagct ttatcaaact gaaagtaatt atgttaatat attggcaaca attattcagt   1440
tatttcaagt accattggaa gaggaaggac aacgtggtgg acctatcctt gcaccagagg   1500
agattaagac tatttttggt agcatcccag atatctttga tgtacacact aagataaagg   1560
atgatcttga agaccttata gttaattggg atgagagcaa aagcattggt gacatttttc   1620
tgaaatattc aaaagatttg gtaaaaacct accctccctt tgtaaacttc tttgaaatga   1680
gcaaggaaac aattatttaa atgtgaaaaa cagaaaccaa gatttcatgc ttttctcaag   1740
ataaaccaag caaaaccaga atgtggacgg cagagccttg ttgaacttct tatccgacca   1800
gtacagaggt tacccagtgt tgcattactt ttaaatgatc ttaagaagca tacagctgat   1860
gaaaatccag cacaaaagca ctttagaaaa agctattgga tcactgaagg aagtaatgac   1920
gcatattaat gaggataaga gaaaaacaga agctcaaaag caaatttttg atgttgttta   1980
tgaagtagat ggatgcccag ctaatctttt atcttctcac cgaagcttag tacagcgggt   2040
tgaaacaatt tctctaggtg agcacccctg tgacagagga gaacaagtaa ctctcttcct   2100
cttcaatgat tgcctagaga tagcaagaaa acggcacaag gttattggca cttttaggag   2160
tcctcatggc caaacccgac cccagcttc tcttaagcat attcacctaa tgcctctttc   2220
tcagattaag aaggtattgg acataagaga gacagaagat tgccataatg cttttgcctt   2280
gcttgtgagg ccaccaacag agcaggcaaa tgtgctactc agtttccaga tgacatcaga   2340
tgaacttcca aaagaaaact ggctaaagat gctgtgtcga catgtagcta acaccatttg   2400
taaagcagat gctgagaatc ttatttatac tgctgatcca gaatcctttg aagtaaatac   2460
aaaagatatg gacagtacat tgagtagagc atcaagagca ataaaaaaga cttcaaaaaa   2520
ggttacaaga gcattctctt tctccaaaac tccaaaaaga gctcttcgaa gggctcttat   2580
gacatcccac ggctcagtgg agggaagaag tccttccagc aatgataagc atgtaatgag   2640
tcgtctttct agcacatcat cattagcagg tatcccttct ccctcccttg tcagccttcc   2700
ttccttcttt gaaaggagaa gtcatacgtt aagtagatct acaactcatt tgatatgaag   2760
cgttaccaaa atcttaaatt atagaaatgt atagacacct catactcaaa taagaaactg   2820
acttaaatgg tacttgtaat tagcacttgg tgaaagctgg aaggaagata aataacacta   2880
aactatgcta tttgattttt cttcttgaaa gagtaaggtt tacctgttac atttcaagt    2940
```

-continued

```
taattcatgt aaaaaatgat agtgattttg atgtaattta tctcttgttt gaatctgtca   3000

ttcaaaggcc aataatttaa gttgctatca gctgatatta gtagctttgc aaccctgata   3060

gagtaaataa attttatggg tgggtgccaa atactgctgt gaatctattt gtatagtatc   3120

catgaatgaa tttatggaaa tagatatttg tgcagctcaa tttatgcaga gattaaatga   3180

catcataata ctggatgaaa acttgcatag aattctgatt aaatagtggg tctgtttcac   3240

atgtgcagtt tgaagtattt aaataaccac tcctttcaca gtttattttc ttctcaagcg   3300

ttttcaagat ctagcatgtg gattttaaaa gatttgccct cattaacaag aataacattt   3360

aaaggagatt gtttcaaaat atttttgcaa attgagataa ggacagaaag attgagaaac   3420

attgtatatt ttgcaaaaac aagatgtttg tagctgtttc agagagagta cggtatattt   3480

atggtaattt tatccactag caaatcttga tttagtttga tagtgtgtgg aattttattt   3540

tgaaggataa gaccatggga aaattgtggt aaagactgtt tgtacccttc atgaaataat   3600

tctgaagttg ccatcagttt tactaatctt ctgtgaaatg catagatatg cgcatgttca   3660

actttttatt gtggtcttat aattaaatgt aaaattgaaa attcatttgc tgtttcaaag   3720

tgtgatatct ttcacaatag ccttttata gtcagtaatt cagaataatc aagttcatat   3780

ggataaatgc atttttattt cctatttctt tagggagtgc tacaaatgtt tgtcacttaa   3840

atttcaagtt tctgttttaa tagttaactg actatagatt gttttctatg ccatgtatgt   3900

gccacttctg agagtagtaa atgactcttt gctacatttt aaaagcaatt gtattagtaa   3960

gaactttgta aataaatacc taaaacccaa gtgtaaaaca tttgtagcac tccctaaaga   4020

aataggaaat aaaaatgcat ttatccatat gaacttgatt attctgaatt actgactata   4080

aaaaggctat tgtgaaagat atcacacttt gaaacagcaa atgaattttc aattttacat   4140

tt                                                                  4142
```

<210> SEQ ID NO 8
<211> LENGTH: 1375
<212> TYPE: DNA
<213> ORGANISM: Homo sapiens

<400> SEQUENCE: 8

```
atgaggggct agctccactg gctttgaggg cctggaaagg cacacaagta ggtccttggc     60

tgaactggtg ccccagccgg acctcgtgtc cctgcactgc tgcagatgca tcagccctcc    120

ccatgttggt gccgctgtca cttcctactg ggatccttcc cctatccagc cacatccagg    180

ctgtgggact acacggtgcc ctgttcccct gggcaggaga agaggtggta cctgcaatgc    240

accttcacag ccaggcaagc attctggatt taccctgtgt aaagaagggt ggtaccctct    300

ttcaggggtg tgatgcagtg cattgatgga gcagctggtg ctgctgggag gccagcctgg    360

aagaggcagc agtggctcaa gtttgcgtgc aggagccaga gtgggaccca cgggctcttg    420

tgggtgtggt ttagaactag atggtgcttt ggggacaagc catccaaaaa ccccaggccc    480

acatccaccc tgatttgata tcccacttcc tgacagatca gaggctgtgt ctttaggcag    540

tggaggtcca ggagcagagc ctggggctgg ttcacagcta aacccctcct tagggcagcc    600

cagagtaggg cctcagctgg caagtccaca agccctgctg ggcccctgc ttgttggcct     660

gacccctccc tcaccaggca gccagccaag gtggttcctg cttcacccac tcagtcatca    720

gcctcaggct gcccaaaatg cctctgacac cagatttata tcttctgggc ggcttcttta    780

aatccagccc ttcacccgcc ccctagagaa gcagtgaaac cccttggcta gtccagctgg    840

aagagctaga ccgcaggagc cgcgccgtct tcctaacctc gcctcggcct tcgctccaca    900
```

```
gtggagagtg ggagcctagc tgtgcttgat gctgaatgcc tgttttgaga gtgtgagtgg     960

gatcatctac agtaaatact tgcaaagcat ggcactgtgg ctctggggag ctggtacgcc    1020

tgtgctgtaa ccatggtact cagtccttcc aaagtgttta ttaatcaagc acctgtcatg    1080

tgccattgag cccacgatgg ggaatgagga cagtccctgc ccccatgaag cttgtgtcct    1140

gttgggagga cagacaggtg gcccagcagt tgcagcatgg tgtgtgcaca cgtttggctg    1200

gtggaaccat gtttctacca ctcatggtca aaaaaagccc accaaagtcc tgggagttca    1260

catctgtgtg atgatacggc aacattgttt gtaatggaaa gactggacac ccccagtgcc    1320

catcagtggg ggagtcatta aataaactat ggtatgtgca cataaaaaaa aaaaa         1375
```

<210> SEQ ID NO 9
<211> LENGTH: 641
<212> TYPE: DNA
<213> ORGANISM: Homo sapiens

<400> SEQUENCE: 9

```
atattattca gccttaaaaa acgatatcct actatttgtc acaacatgga tggacctgga      60

agaccttata ctagatgata taagccagac acagaaagaa aagtgatttc acttatatgt     120

agaatatata taaaagaaaa agctcaaaaa cacagagaat aaaacatggc gaccatggta     180

gggaacagga ggaggaaaca gagatatagg tcaaaggata caaaatagca gatatgcaga     240

atgaacaagt gtagagagtt aatgtataac atgaggacta aggttaataa aattgtatta     300

gggattttgt taactaagta gattttagct gcttttgtca caaaaagtag ttgtgtgaga     360

atgatagata tgtaaatctg cttccctaca gtaaccattt tattatttct atgcatccca     420

aactaccatg ttgtaaacct caaatataca caataaaatg tatttaaaaa acaaaataga     480

gcttgtctcg atcaggactg gcttttgtgt accaaaaggc aaaaaaaaaa aacaaaaaca     540

aaaccctgtt ttcagtgtta tgggagagaa atgaacaatg ggaaacaacc aaggaaagct     600

ggagcaggtt acgtataaaa ataaagtccc tcgaagccga a                         641
```

<210> SEQ ID NO 10
<211> LENGTH: 4689
<212> TYPE: DNA
<213> ORGANISM: Homo sapiens

<400> SEQUENCE: 10

```
gtggacccag ggtggggaac tacctcttcc tctccacgcg gttgagaaga ccggtcggcc      60

tgggcaacct gcgctgaaga tgccgggaaa actccgtagt gacgctggtt tggaatcaga     120

caccgcaatg aaaaaagggg agacactgcg aaagcaaacc gaggagaaag agaaaaaaga     180

gaagccaaaa tctgataaga ctgaagagat agcagaagag gaagaaactg ttttccccaa     240

agctaaacaa gttaaaaaga aagcagagcc ttctgaagtt gacatgaatt ctcctaaatc     300

caaaaaggca aaaaagaaag aggagccatc tcaaaatgac atttctccta aaaccaaaag     360

tttgagaaag aaaaaggagc ccattgaaaa gaaagtggtt tcttctaaaa ccaaaaaagt     420

gacaaaaaat gaggagcctt ctgaggaaga aatagatgct cctaagccca agaagatgaa     480

gaaagaaaag gaaatgaatg gagaaactag agagaaaagc cccaaactga agaatggatt     540

tcctcatcct gaaccggact gtaaccccag tgaagctgcc agtgaagaaa gtaacagtga     600

gatagagcag gaaatacctg tggaacaaaa agaaggcgct ttctctaatt ttcccatatc     660

tgaagaaact attaaacttc tcaaaggccg aggagtgacc ttcctatttc ctatacaagc     720
```

-continued

```
aaagacattc catcatgttt acagcgggaa ggacttaatt gcacaggcac ggacaggaac    780
tgggaagaca ttctcctttg ccatcccttt gattgagaaa cttcatgggg aactgcaaga    840
caggaagaga ggccgtgccc ctcaggtact ggttcttgca cctacaagag agttggcaaa    900
tcaagtaagc aaagacttca gtgacatcac aaaaaagctg tcagtggctt gtttttatgg    960
tggaactccc tatggaggtc aatttgaacg catgaggaat gggattgata tcctggttgg   1020
aacaccaggt cgtatcaaag accacataca gaatggcaaa ctagatctca ccaaacttaa   1080
gcatgttgtc ctggatgaag tggaccagat gttggatatg ggatttgctg atcaagtgga   1140
agagatttta agtgtggcat acaagaaaga ttctgaagac aatccccaaa cattgctttt   1200
ttctgcaact tgccctcatt gggtatttaa tgttgccaag aaatacatga aatctacata   1260
tgaacaggtg gacctgattg gtaaaaagac tcagaaaacg gcaataactg tggagcatct   1320
ggctattaag tgccactgga ctcagagggc agcagttatt ggggatgtca tccgagtata   1380
tagtggtcat caaggacgca ctatcatctt ttgtgaaacc aagaaagaag cccaggagct   1440
gtcccagaat tcagctataa agcaggatgc tcagtccttg catggagaca ttccacagaa   1500
gcaaagggaa atcaccctga aaggttttag aaatggtagt tttggagttt tggtggcaac   1560
caatgttgct gcacgtgggt tagacatccc tgaggttgat ttggttatac aaagctctcc   1620
accaaaggat gtagagtcct acattcatcg atccgggcgg acaggcagag ctggaaggac   1680
gggggtgtgc atctgctttt atcagcacaa ggaagaatat cagttagtac aagtggagca   1740
aaaagcggga attaagttca aacgaatagg tgttccttct gcaacagaaa taataaaagc   1800
ttccagcaaa gatgccatca ggcttttgga ttccgtgcct cccactgcca ttagtcactt   1860
caaacaatca gctgagaagc tgatagagga gaagggagct gtggaagctc tggcagcagc   1920
actggcccat atttcaggtg ccacgtccgt agaccagcgc tccttgatca actcaaatgt   1980
gggttttgtg accatgatct tgcagtgctc aattgaaatg ccaaatatta gttatgcttg   2040
gaaagaactt aaagagcagc tgggcgagga gattgattcc aaagtgaagg gaatggtttt   2100
tctcaaagga aagctgggtg tttgctttga tgtacctacc gcatcagtaa cagaaataca   2160
ggagaaatgg catgattcac gacgctggca gctctctgtg gccacagagc aaccagaact   2220
ggaaggacca cgggaaggat atggaggctt caggggacag cgggaaggca gtcgaggctt   2280
caggggacag cgggacggaa acagaagatt cagaggacag cgggaaggca gtagaggccc   2340
gagaggacag cgatcaggag gtggcaacaa aagtaacaga tcccaaaaca aaggccagaa   2400
gcggagtttc agtaaagcat ttggtcaata attagaaata gaagatttat atagcaaaaa   2460
gagaatgatg tttggcaata tagaactgaa cattattttt catgcaaagt taaaagcaca   2520
ttgtgcctcc ttttgaccac ttgccaagtc cctgtctctt tcagacacag acaagcttca   2580
tttaaattat ttcatctgat cattatcatt tataacttta ttgttacttc ttcatcagtt   2640
tttccttttg aaaggtgtat gaattcatta catttttatt ctaatgtatt atctgtagat   2700
tagaagataa aatcaagcat gtatctgcct atactttgtg agttcacctg tctttatact   2760
caaaagtgtc ccttaatagt gtccttccct gaaataaata cctaagggag tgtaacagtc   2820
tctggaggac cactttgagc ctttggaagt taaggtttcc tcagccacct gccgaacagt   2880
ttctcatgtg gtcctattat ttgtctactg agacttaata ctgagcaatg ttttgaaaca   2940
agatttcaaa ctaatctggg ttgtaataca gtttatacca gtgtatgctc tagacttgga   3000
agatgtagta tgtttgatgt ggattaccta tacttatgtt cgttttgata catttttagc   3060
ttctcattat aaggtgattc atgctttagt gaattcttca tagatagtat atataaaagt   3120
```

-continued

```
acattttaat agaaagccag ggttttaagg aatttcacat gtataaggtg gctccatagc   3180
tttatttgta agtaggctgg ataaatggtg cttaaatggt aatgtactcc acttcttcct   3240
attggaagat taacattatt taccaagaag gacttaaggg agtaaggggc gcagattagc   3300
attgctcaag agtatgtaaa aaaaaaaaaa aaaaaaggac ccaaaccact ggaaataatc   3360
aaatgcaaaa aggtaacaaa ttcataactg gaaagcaaag agaagaacaa gtatgatttg   3420
gatgataaag cattgtttta atggtgaaaa cttcacagat cactaatgtt tctagaggtt   3480
aacttcaagt gggcaagctg gggtttttag gtagtcagtg gcctagttcc taaagccaca   3540
gtataggatc tgttaaactg aatgtctgtt gaaagtttgt tttagctgct tggaggcttc   3600
cttttaagac aaactgtatg tgattaagtt gttttgaggg aactgaagaa cctgatgtag   3660
cccctggcca gataactgcc tgatttctca gatattattt ctctgggaaa cattctacat   3720
agcacaggag cttaagagtg gcattatctt ctcgccttaa tttccagaga ttatttctgt   3780
actgagaatc ctggaactac tatgctagga aatttaaagc tgcatggtct gtcttgtttt   3840
catttaatta ttgtgaatac ctagaatctt tcttggtcct gatttctctt gcttaatcca   3900
gtctttatct ctaactgccc cttatttgat caccatgtac taggagctct gatagccagc   3960
tcagctccta atccttgagg caacattctt tttctatttg aacttcagtt ctgtccttga   4020
atcccgacta gatatttctt gccctctggt ctcagaattc tcttggcttt tattccttga   4080
tccacttgcc agttttatca ctttaccctt gttcctcatg gcttcccatc aagccatggg   4140
tattaggtga cagtgtaatt tattagattc tggttttgcc caaatactgg gcatgcttta   4200
ataataactg aaccatttca ttatttggat aggcatgggt accttatcaa gcagattaaa   4260
aggatatggt acccgtcctt tagaaaagaa cagctaaaac cttgttgtgg attatggatt   4320
tagcctaaag aaaaataatc tggcataaat taagagtaag agagaagatt aatagaaatt   4380
tcacttcaca taacttaaaa catggctatt tcaataaagg actaaagttt ctcctggatc   4440
ccagaattca acctgtattt ataaatgtat aatgtattta gctacttttt ggtttaaatg   4500
aacttgttgg gttagcttgg taaatgttat aatttttact attttctaca aagaaaatat   4560
tttctaattt aagttggagc tatctgtgca gcagtttctc tacagttgtg cataaatgtt   4620
tttactataa aatgagctaa tgtataaaat actgctgtat accataataa agatagtaat   4680
acttgaaaa                                                           4689
```

<210> SEQ ID NO 11
<211> LENGTH: 1564
<212> TYPE: DNA
<213> ORGANISM: Homo sapiens

<400> SEQUENCE: 11

```
ctgtcaatga tggatctcag aaatacccca gccaaatctc tggacaagtt cattgaagac     60
tatctcttgc cagacacgtg tttccgcatg caaatcaacc atgccattga catcatctgt    120
gggttcctga aggaaaggtg cttccgaggt agctcctacc ctgtgtgtgt gtccaaggtg    180
gtaaaggatc agttaaatcg ccggggagag ttcatccagg aaattaggag acagctggaa    240
gcctgtcaaa gagagagagc attttccgtg aagtttgagg tccaggctcc acgctggggc    300
aacccccgtg cgctcagctt cgtactgagt tcgctccagc tcggggaggg ggtggagttc    360
gatgtgctgc ctgcctttga tgccctgggt cagttgactg gcagctataa acctaacccc    420
caaatctatg tcaagctcat cgaggagtgc accgacctgc agaaagaggg cgagttctcc    480
```

-continued

```
acctgcttca cagaactaca gagagacttc ctgaagcagc gccccaccaa gctcaagagc    540
ctcatccgcc tagtcaagca ctggtaccaa aattgtaaga agaagcttgg gaagctgcca    600
cctcagtatg ccctggagct cctgacggtc tatgcttggg agcgagggag catgaaaaca    660
catttcaaca cagcccaggg atttcggacg gtcttggaat tagtcataaa ctaccagcaa    720
ctctgcatct actggacaaa gtattatgac tttaaaaacc ccattattga aaagtacctg    780
agaaggcagc tcacgaaacc caggcctgtg atcctggacc cggcggaccc tacaggaaac    840
ttgggtggtg gagacccaaa gggttggagg cagctggcac aagaggctga ggcctggctg    900
aattacccat gctttaagaa ttgggatggg tccccagtga gctcctggat tctgctggct    960
gaaagcaaca gtgcagacga tgagaccgac gatcccagga ggtatcagaa atatggttac   1020
attggaacac atgagtaccc tcatttctct catagaccca gcacactcca ggcagcatcc   1080
accccacagg cagaagagga ctggacctgc accatcctct gaatgccagt gcatcttggg   1140
ggaaagggct ccagtgttat ctggaccagt tccttcattt tcaggtggga ctcttgatcc   1200
agagaggaca aagctcctca gtgagctggt gtataatcca ggacagaacc caggtctcct   1260
gactcctggc cttctatgcc ctctatccta tcatagataa cattctccac agcctcactt   1320
cattccacct attctctgaa aatattccct gagagagaac agagagattt agataagaga   1380
atgaaattcc agccttgact ttcttctgtg cacctgatgg gagggtaatg tctaatgtat   1440
tatcaataac aataaaaata aagcaaatac catttattgg gtgtttatta acttcaaggc   1500
acagagccaa gaagtacaga tgcatatcta ggggtattgt gtgtgtatat acattgattc   1560
aaca                                                                1564
```

```
<210> SEQ ID NO 12
<211> LENGTH: 2181
<212> TYPE: DNA
<213> ORGANISM: Homo sapiens

<400> SEQUENCE: 12
```

```
ggggaccaag aagcagcttc tccgctcctt ctaggatctc cgcctggttc ggcccgcctg     60
cctccactcc tgcctccacc atgtccatca gggtgaccca gaagtcctac aaggtgtcca    120
cctctggccc ccgggccttc agcagccgct cctacacgag tgggcccggt tcccgcatca    180
gctcctcgag cttctcccga gtgggcagca gcaactttcg cggtggcctg ggcggcggct    240
atggtggggc cagcggcatg ggaggcatca ccgcagttac ggtcaaccag agcctgctga    300
gccccccttgt cctggaggtg gaccccaaca tccaggccgt gcgcacccag gagaaggagc    360
agatcaagac cctcaacaac aagtttgcct ccttcataga caaggtacgg ttcctggagc    420
agcagaacaa gatgctggag accaagtgga gcctcctgca gcagcagaag acggctcgaa    480
gcaacatgga caacatgttc gagagctaca tcaacaacct taggcggcag ctggagactc    540
tgggccagga gaagctgaag ctggaggcgg agcttggcaa catgcagggg ctggtggagg    600
acttcaagaa caagtatgag gatgagatca ataagcgtac agagatggag aacgaatttg    660
tcctcatcaa gaaggatgtg gatgaagctt acatgaacaa ggtagagctg gagtctcgcc    720
tggaaggggc tgaccgacga gatcaacttc ctcaggcagc tgtatgaaga ggagatccgg    780
gagctgcagt cccagatctc ggacacatct gtggtgctgt ccatggacaa cagccgctcc    840
ctggcacatg gacagcatca ttgctggagg tcaaggcaca gtacgaggat attgccaacc    900
gcagccgggc tgaggctgag agcatgtacc agatcaagta tgaggagctg cagagcctgg    960
ctgggaagca cggggatgac ctgcggcgca caaagactga gatctctgag atgaaccgga   1020
```

-continued

```
acatcagccg gctccaggct gagattgagg gcctcaaagg ccagagggct tccctggagg   1080
ccgccattgc agattgccga gcagccgtgg agagctggcc attaaggatg ccaacgccaa   1140
gttgtccgag ctggaggccg ccctgcaggc gggccaagca ggacatggcg cggcagctgc   1200
gtgagtacca ggagctgatg aacgtcaagc tggccctgga catcgagatc gccacctaca   1260
ggaagctgct ggagggcgag gagagccggc tggagtctgg gatgcagaac atgagtattc   1320
atacgaagac caccagcggc tatgcaggtg gtctgagcct cggcctatgg gggcctcaca   1380
agccccggcc tcagctacag cctgggctcc agctttggct ctggcgcggg ctccagctcc   1440
ttcagccgca ccagctcctc cagggccgtg gttgtgaaga agatcgagac acgtgatggg   1500
aagctggtgt ctgagtcctc tgacgtcctg cccaagtgaa cagctgcggc agcccctccc   1560
agcctacccc tcctgcgctg ccccagagcc tgggaaggag gccgctatgc agggtagcac   1620
tgggaacagg agacccacct gaggctcagc cctagccctc agcccacctg ggagtttac   1680
tacctgggga ccccccttgc ccatgcctcc agctacaaaa caattcaatt gcttttttt   1740
tttggtccaa aataaaacct cagctagctc tgccaaaaaa aaaaaagaat aaaaagaaaa   1800
aaattggggg cactaacacg aggacggaaa caaagagaaa gtgaagggga cacggtgaca   1860
aaggagaaca tgaacacaaa tccgggcaca aggggagaac cgacggatcc caaaaagcag   1920
cacaatcacg cgaaagccgt gatacctgta gaagcgacgc aacagaagaa gaaaagaaga   1980
gagaagagac gcaaacgaag aggcacaaac agcagcaaaa gaaagaagaa cgacgacgaa   2040
catagacgaa ccaacccaca gagacccgaa tagagcaaaa cagacacaag aaaaacagaa   2100
gacaaggaaa ggcagaagaa agcaaaagag agacagcaag aagacagaca agaacagggg   2160
gacacagtta gcaacgaaaa a                                              2181
```

<210> SEQ ID NO 13
<211> LENGTH: 899
<212> TYPE: DNA
<213> ORGANISM: Homo sapiens
<220> FEATURE:
<221> NAME/KEY: unsure
<222> LOCATION: (368)..(388)
<221> NAME/KEY: unsure
<222> LOCATION: (446)..(547)

<400> SEQUENCE: 13

```
gggagaggct ccgtgacgtc cccagggccc cagaacgagg aaggagcgga gttgggattc     60
cagcccagtt ggacgctgaa gtccctgttt tgtttactgc ctcctgttca tggcgtatga    120
atgtatctga gatgctttgt aaggcataaa gtgcaatact agcttagtgg ctgttcgttc    180
agtgattcct tctgttacca aacaggtggc tgagatgaga gggcaaccca agcctaacgc    240
ccttcagtgg ccttgcatca gagtactcgt gacaggtacc tctccgtgga gaggggctgt    300
cctctgccct tgcctgctcc tcctattgca acagtcctgt ggactagctc aggctctaca    360
ggggctgnnn nnnnnnnnnn nnnnnnnngt gtatatgtgt ctacctacac acaagcacat    420
gtgcacacat gcacacacat gcatgnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnncag gcacacacat acatgcaggt gtgcagactt ggctccaggc gtgtgtttga    600
tagtattatt ctatgatatt tccctcatct ccatagaata ccagcttctg aatcctcaat    660
cagcctttac tgcaagaaga aaagaaaaac ctctctcatt ccaggtctgt ggtgcagatg    720
ggaagagtat agtcaaaacc cattaaggcc ttagtcaaat gccagccgaa ttagaacgca    780
```

atgaacgtta gacaaaacaa cccaactggc caggcggggg aggcgcagag cgtataaata 840
taaagttaga tacttataaa gaataaagac tctaataaaa tattttatat aaaactttt 899

<210> SEQ ID NO 14
<211> LENGTH: 1554
<212> TYPE: DNA
<213> ORGANISM: Homo sapiens
<220> FEATURE:
<221> NAME/KEY: unsure
<222> LOCATION: (1544)

<400> SEQUENCE: 14
cccacgcgtc cgctcacctc cgagccacct ctgctgcgca ccgcagcctc ggacctacag 60
cccaggatac tttgggactt gccggcgctc agaaacgcgc ccagacggcc cctccacctt 120
ttgtttgcct agggtcgccg agagcgcccg gagggaaccg cctggccttc ggggaccacc 180
aattttgtct ggaaccaccc tcccggcgta tcctactccc tgtgccgcga ggccatcgct 240
tcactggagg ggtcgatttg tgtgtagttt ggtgacaaga tttgcattca cctggcccaa 300 acccttttg tctctttggg tgaccggaaa actccacctc aagttttctt ttgtgggggc 360
tgccccccaa gtgtcgtttg ttttactgta gggtctcccc gcccggcgcc cccagtgttt 420
tctgagggcg gaaatggcca attcgggcct gcagttgctg ggcttctcca tgggccctgc 480
tgggctgggt gggtctggtg gcctgcaccg ccatcccgca gtggcagatg agctcctatg 540
cgggtgacaa catcatcacg gcccaggcca tgtacaaggg gctgtggatg gactgcgtca 600
cgcagagcac ggggatgatg agctgcaaaa tgtacgactc ggtgctcgcc ctgtccgcgg 660
ccttgcaggc cactcgagcc ctaatggtgg tctccctggt gctgggcttc ctggccatgt 720
ttgtggccac gatgggcatg aagtgcacgc gctgtggggg agacgacaaa gtgaagaagg 780
cccgtatagc catgggtgga ggcataattt tcatcgtggc aggtcttgcc gccttggtag 840
cttgctcctg gtatggccat cagattgtca cagactttta taaccctttg atccctacca 900
acattaagta tgagtttggc cctgccatct ttattggctg ggcagggtct gccctagtca 960
tcctgggagg tgcactgctc tcctgttcct gtcctgggaa tgagagcaag gctgggtacc 1020
gtgtaccccg ctcttaccct aagtccaact cttccaagga gtatgtgtga cctgggatct 1080
ccttgcccca gcctgacagg ctatgggagt gtctagatgc ctgaaagggc ctggggctga 1140
gctcagcctg tgggcagggt gccggacaaa ggcctcctgg tcactctgtc cctgcactcc 1200
atgtatagtc ctcttgggtt gggggtgggg gggtgccgtt ggtgggagag acaaaaagag 1260
ggagagtgtg ctttttgtac agtaataaaa aataagtatt gggaagcagg ctttttttccc 1320 ttcagggcct ctgctttcct cccgtccaga tccttgcagg gagcttggaa ccttagtgca 1380
cctacttcag ttcagaacac ttagcacccc actgactcca ctgacaattg actaaaagat 1440
gcaggtgctc gtatctcgac attcattccc acccccctct tatttaaata gctaccaaag 1500
tacttctttt ttaataaaaa aataaagatt tttattaggt aaanaaaaaa aaaa 1554

<210> SEQ ID NO 15
<211> LENGTH: 4174
<212> TYPE: DNA
<213> ORGANISM: Homo sapiens

<400> SEQUENCE: 15
atggcgtgca agtatccgct gcggtgttct ggtgctagag tggagaggct ggcaaagaag 60
aaggcacacg catgttggta caagtttgct atggacagca accatcaaag taattacaaa 120

-continued

```
ctcagtaaaa ctgagaagaa gttcttaagg aaacagatta aagccaagca tactttgctg    180
agacatgaag gcattgagac agtatcctat gccactcaga gcctggttgt tgccaatggt    240
ggtttgggta atggtgtgag tcggaaccag ctgctcccgg ttttagagaa atgtggactg    300
gtggatgctc tcttaatgcc acctaacaag ccgtactcat ttgcaagata cagaactaca    360
gaagaatcta agagagccta tgttaccctc aatggaaaag aagtagtgga tgatttagga    420
caaaagatca ctctgtattt gaattttgtg gaaaaagtgc agtggaagga gttgaggcct    480
caagccttac caccaggact catggtagta gaagaaataa tttcttctga ggaggagaaa    540
atgcttttgg aaagtgttga ttggacagaa gatacagaca atcaaaactc tcaaaaatcc    600
ttaaaacaca gaagagtaaa gcattttggt tatgagttcc actatgagaa caacaatgta    660
gataaagata agccattatc tgggggtctt cctgacattt gtgaaagctt tttggagaaa    720
tggttgagga aaggttacat taaacataaa cctgatcaaa tgaccataaa tcagtatgaa    780
cctgggcaag gaattcccgc tcatattgat acacattccg cttttgagga tgagatcgtt    840
tctctcagtt tggggtcaga gattgtcatg gattttaagc acccagatgg cattgcagtg    900
ccagttatgt tgcctcgtcg gagtttgctg gtgatgacag gagaatctag ataccctttgg    960
acccatggaa tcacgtgcag aaaatttgat actgttcaag catctgagag tcttaaaagt   1020
ggaattatca ccagtgatgt tggagactta actttaagca agaggggact acgaacatca   1080
tttacattta ggaaagtgag gcaaacacct tgtaactgta gttacccgtt ggtctgtgat   1140
agccagagga aagagactcc cccctcattt ccagagagtg ataaagaagc ctcacggctg   1200
gagcaagagt acgtccatca ggtttatgaa gagattgctg ggcacttcag cagcacaaga   1260
catacccctt ggccgcacat tgtggagttt ttgaaggctt tgccaagtgg ttcaatagtg   1320
gctgatattg gatgtggtaa tggaaagtat cttggcatca ataaggagtt atatatggca   1380
aatgaggaaa cagaggcttt gagatatggc tgtcctaatt tacattccca ccaacagtat   1440
gccaggattc ccttttcccc acatcctcaa cgccgtttgt tatcttttgt ctctttgata   1500
atggccagat ctaacaagtg tgagattggt tgtgatcgta gccaaaacct tgtggacatt   1560
tgtagagaga ggcaatttca ggcttttgtc tgtgatgcat tggcagtacc agtccgcagt   1620
gggtcttgtg atgcctgcat ctccattgct gttattcatc attttgcaac agcagagcgt   1680
agagtggcag ctctccaaga aattgttcga ctcctgagac caggtgggaa ggcactcatt   1740
tatgtctggg caatggaaca agaatataat aagcagaagt ccaagtatct tagaggaaac   1800
agaaatagcc aaggaaagaa agaggagatg aacagtgata cctcagtgca gaggtcactt   1860
gtggagcaaa tgcgtgacat gggcagtcga gactcggcat cttctgtccc ccgcattaat   1920
gactctcagg aaggaggatg taattcaagg caagtttcta attccaagct gcctgttcat   1980
gttaacagga cttcttttta ttctcaagat gtactggttc cctggcacct taagggaaat   2040
cctgataaag gcaaacctgt tgagccattt ggtcccatag gatcccagga cccaagtcct   2100
gtgtttcatc gttactacca tgtgttccgt gagggagaac tggaaggtgc ctgcaggact   2160
gtgagtgatg tcagaattct gcaaagctac tacgatcaag gaaactggtg tgtgattctt   2220
caaaaggcct gattatttac ctgaacacat catatataaa gaagaaatgc tcacttaaaa   2280
aaaaaagaga gaataaatta attacccttt taattaaaga gaaaacttgt gggaaagtac   2340
caaaggaaag ctgagaaaaa tttggaagta gggattcatt aggagacatt caaatgtctc   2400
ctgttggctg acatcacaga tgtggtgttg gctcctccta cttccctagg agaggtggtt   2460
```

-continued

```
tctaaaagtg attgaagcag tttgtgcagt gtttgtaatt cttgggtaag agcccaagga   2520
ttttgaagat aatagttttt tagtaaagtg ctactaaatg tagtaaatca tgtaggattt   2580
tagggatgta attatatgtt aatacagaaa atagtcctgg tcaatagaaa attgtctgaa   2640
gttttaccta tgatttttag ctctgtaaaa tcatagacaa taaccattct atttccatgc   2700
ctgactagcc cagggctgga cgtatagcgg gtgtccaata acgtttagtc aatcagataa   2760
tacccagaac ttagtaggag tttcattcaa aaactatttt ttgaacccaa ccatgtacca   2820
gttactattt taagtactga taatgaagca gtgaataaga aagagcaaag ctcttgccct   2880
tatggtgctt acattctaga cggggagaca gacagcaggc aaatcaataa atagatacta   2940
tgtgccagat agtgataaat gccatgaaaa acataaaatg agagacgatt caccttggag   3000
caaaagatta cttttaagtg actgaaataa ctactaatcc tgactaattt attatcaaga   3060
gttaattggt attccaaatt cattgagcag ggtgctaaaa acaacccaaa tgtgctcctt   3120
taactccttt gtttaaatga caaaagttag aatgtggtca ctcagaccta actgtgccct   3180
tagagccaaa gctgtggtgt cattattggt tatttctagt tgattcatag tttgtcccaa   3240
tccaggttca atcgggttat ttttaagatc tgtacaatat tgcataatag taacccagtt   3300
aacttaccac ttaggttaga tttcctggag gaacaaaggt agaaattcaa ccataggtca   3360
aattatcaca tagaaggaaa aggctttttt tcaaagaaaa aattttttga acactttact   3420
cccagtatgc attacttttg tagtagtaat gcttaagact gttttaaaga aaaattgctt   3480
tctgtttaat taatgtttac tgttattaat gctagtgata cttaatcttg aagcatcaag   3540
ttttcagaaa cctatagtga tcaataatgg gtctcagatg agaggatgat tattttttc    3600
atggaatttc agtccaacat cctggtgtac tggtccctct gggatgaatt tataaggctc   3660
atgatatagg aaaaggaata tagggctaaa aatagtttta tttctgatat aaattctggt   3720
acttgacacc aaagtttgaa gtcaagtcat gccaataaat tttaacatcc aaatgaaata   3780
gatgattttc tatgaagatg aaaaatacca aaattgactc aagaagggag agaaaatgga   3840
agatgttgaa aaatagcata ggaattcaga actgggctct agaatcagat ttcctgagag   3900
ttgaattcta gatctgccat ttattagctg tgggattttg ggcaaatttc ttgactttct   3960
gtgcttcagt tttcttagct gtaaaattgg aagagttgtt atgaaaattc actgaaagta   4020
tatttgtata catcatagga tagtgtaaga atatagtatg gctttgagaa atgttcatta   4080
ttattactcc cagaggagtt ttaggtatta agtgatgcca aatataattt gttaattgta   4140
taataaaaat ctatattctt actgaaaaaa aaaa                               4174
```

```
<210> SEQ ID NO 16
<211> LENGTH: 462
<212> TYPE: DNA
<213> ORGANISM: Homo sapiens
<220> FEATURE:
<221> NAME/KEY: unsure
<222> LOCATION: (323)
<221> NAME/KEY: unsure
<222> LOCATION: (358)
<221> NAME/KEY: unsure
<222> LOCATION: (428)

<400> SEQUENCE: 16

tcttggtgac gtctcgtggc tggcaccgct tggttcttcc cgtggcccgt ggcctcctgg     60
cgagtggctg gccctgcagt ggatagagca ccaggagggc cggcacgtgg ggcagagggg    120
gcggggcttg gaggaagagg tgagccgagg caggtgaatg tcaaacctcc acagactgaa    180
```

-continued

```
tctggttcat ctgcgcccgc atcacctgga tactgttcag gattttttttc tggtggccag    240

ccaaagtgac cccaacccgg agaatgtcct ccatcatcat ctgagacacg acgtcaaagg    300

aggtgaagcc ggcattggcg aantctcctt gtactgcccc atcttgatgg cctccaanca    360

ctcgtccacc gtgttaaact ggtgtagtcg gggatcgtgc ggtccagcag cggcaggttg    420

atgcaganga gaagggcgcc atggctttga agctgttggg at                       462
```

<210> SEQ ID NO 17
<211> LENGTH: 3219
<212> TYPE: DNA
<213> ORGANISM: Homo sapiens

<400> SEQUENCE: 17

```
cccgggggct gcggtgctca aaggggcaag agctgagcgg aacaccggcc cgccgtcgcg     60

gcagctgctt cacccctctc tctgcagcca tggggctccc tcgtggacct ctcgcgtctc    120

tcctccttct ccaggtttgc tggctgcagt gcgcggcctc cgagccgtgc cgggcggtct    180

tcagggaggc tgaagtgacc ttggaggcgg gaggcgcgga gcaggagccc ggccaggcgc    240

tggggaaagt attcatgggc tgccctgggc aagagccagc tctgtttagc actgataatg    300

atgacttcac tgtgcggaat ggcgagacag tccaggaaag aaggtcactg aaggaaagga    360

atccattgaa gatcttccca tccaaacgta tcttacgaag acacaagaga gattgggtgg    420

ttgctccaat atctgtccct gaaaatggca agggtccctt cccccagaga ctgaatcagc    480

tcaagtctaa taaagataga gacaccaaga ttttctacag catcacgggg ccgggggcag    540

acagcccccc tgagggtgtc ttcgctgtag agaaggagac aggctggttg ttgttgaata    600

agccactgga ccgggaggag attgccaagt atgagctctt tggccacgct gtgtcagaga    660

atggtgcctc agtggaggac cccatgaaca tctccatcat cgtgaccgac cagaatgacc    720

acaagcccaa gtttacccag gacaccttcc gagggagtgt cttagaggga gtcctaccag    780

gtacttctgt gatgcaggtg acagccacag atgaggatga tgccatctac acctacaatg    840

gggtggttgc ttactccatc catagccaag aaccaaagga cccacacgac ctcatgttca    900

caattcaccg gagcacaggc accatcagcg tcatctccag tggcctggac cgggaaaaag    960

tccctgagta cacactgacc atccaggcca cagacatgga tggggacggc tccaccacca   1020

cggcagtggc agtagtggag atccttgatg ccaatgacaa tgctcccatg tttgaccccc   1080

agaagtacga ggcccatgtg cctgagaatg cagtgggcca tgaggtgcag aggctgacgg   1140

tcactgatct ggacgccccc aactcaccag cgtggcgtgc cacctacctt atcatgggcg   1200

gtgacgacgg ggaccatttt accatcacca cccaccctga gagcaaccag ggcatcctga   1260

caaccaggaa gggtttggat tttgaggcca aaaaccagca caccctgtac gttgaagtga   1320

ccaacgaggc cccttttgtg ctgaagctcc caacctccac agccaccata gtggtccacg   1380

tggaggatgt gaatgaggca cctgtgtttg tcccaccctc caaagtcgtt gaggtccagg   1440

agggcatccc cactggggag cctgtgtgtg tctacactgc agaagaccct gacaaggaga   1500

atcaaaagat cagctaccgc atcctgagag acccagcagg gtggctagcc atggacccag   1560

acagtgggca ggtcacagct gtgggcaccc tcgaccgtga ggatgagcag tttgtgagga   1620

acaacatcta tgaagtcatg gtcttggcca tggacaatgg aagccctccc accactggca   1680

cgggaaccct tctgctaaca ctgattgatg tcaacgacca tggcccagtc cctgagcccc   1740

gtcagatcac catctgcaac caaagccctg tgcgccaggt ggctgaacat cacggacaag   1800

gacctgtctc cccacacctc ccctttccag gcccagctca cagatgactc agacatctac   1860
```

```
tggacggcag aggtcaacga ggaaggtgac acagtggtct tgtccctgaa gaagttcctg   1920

aagcaggata catatgacgt gcacctttct ctgtctgacc atggcaacaa agagcagctg   1980

acggtgatca gggccactgt gtgcgactgc catggccatg tcgaaacctg ccctggaccc   2040

tggaagggag gtttcatcct ccctgtgctg gggctgtcc tggctctgct gttcctcctg   2100

ctggtgctgc ttttgttggt gagaaagaag cggaagatca aggagcccct cctactccca   2160

gaagatgaca cccgtgacaa cgtcttctac tatggcgaag agggggtgg cgaagaggac   2220

caggactatg acatcaccca gctccaccga ggtctggagg ccaggccgga ggtggttctc   2280

cgcaatgacg tggcaccaac catcatcccg acacccatgt accgtcctag gccagccaac   2340

ccagatgaaa tcggcaactt tataattgag aacctgaagg cggctaacac agaccccaca   2400

gccccgccct acgacaccct cttggtgttc gactatgagg gcagcggctc cgacgccgcg   2460

tccctgagct ccctcacctc ctccgcctcc gaccaagacc aagattacga ttatctgaac   2520

gagtggggca gccgcttcaa gaagctggca gacatgtacg gtggcgggga ggacgactag   2580

gcggcctgcc tgcagggctg ggaccaaac gtcaggccac agagcatctc caaggggtct   2640

cagttccccc ttcagctgag gacttcggag cttgtcagga agtggccgta gcaacttggc   2700

ggagacaggc tatgagtctg acgttagagt ggttgcttcc ttagcctttc aggatggagg   2760

aatgtgggca gtttgacttc agcactgaaa acctctccac ctgggccagg gttgcctcag   2820

aggccaagtt tccagaagcc tcttacctgc cgtaaaatgc tcaaccctgt gtcctgggcc   2880

tgggcctgct gtgactgacc tacagtggac tttctctctg gaatggaacc ttcttaggcc   2940

tcctggtgca acttaatttt tttttttaat gctatcttca aaacgttaga gaaagttctt   3000

caaaagtgca gcccagagct gctgggccca ctggccgtcc tgcatttctg gtttccagac   3060

cccaatgcct cccattcgga tggatctctg cgtttttata ctgagtgtgc ctaggttgcc   3120

ccttattttt tattttccct gttgcgttgc tatagatgaa gggtgaggac aatcgtgtat   3180

atgtactaga acttttttat taaagaaact tttcccaga                          3219
```

<210> SEQ ID NO 18
<211> LENGTH: 541
<212> TYPE: DNA
<213> ORGANISM: Homo sapiens
<220> FEATURE:
<221> NAME/KEY: unsure
<222> LOCATION: (524)

<400> SEQUENCE: 18

```
gaattctgga caagggatgt gaaaattcca gaaaccctcg attgtgacca aaatgactgt     60

aaaatatgga gcacagcctg tcactatatg aatataaatg gcctttggca agaggtaagt    120

tctttggaaa gaatggtctc cagctatatg tctcaagctt catggagagg ggcagggatg    180

aatggcaggg aggaagcagg aggtctcacc agcagaatcc aggagctcac tggggaccca    240

tcccaattct taaagcatgg gtaattcagc caggcctcag cctcttgtgc cagctgcctc    300

caaccctttg ggtctccacc acccaagttt cctgtagggt ccgccgggtc caggatcaca    360

ggcctgggtt tcgtgagctg ccttctcagg tacttttcaa taatggggtt tttaaagtca    420

taatactttg tccagtagat gcagagttgc tggtagttta tgactaattc caagaccgtc    480

cgaaatccct ggggctgtgt tgaaatgtgt ttcatgctcc tcgntcccaa gcatagaccg    540

t                                                                    541
```

-continued

<210> SEQ ID NO 19
<211> LENGTH: 3174
<212> TYPE: DNA
<213> ORGANISM: Homo sapiens

<400> SEQUENCE: 19

```
gtttggtatc ttgtttccat agctgccaaa tatgaatctg aaaacagggt gggtagctaa     60
ggtcattcct cctgggtttt agtggcattg gctttccttc actaaagctc cctttttttt    120
ctgttggcaa ggacaggtta cagaatagga agagtagcac tttccgccta agcactttag    180
gaaatcacct ttctaagccc tggggcgccc aagtcccatg ggacagggaa acgtggtcct    240
cagtgaggct gctgcctggc tggcccggag tcctccctag gagaggggct cgatgggctg    300
ggggaaggag cctgaaggtt gcccctggtt gcatcccaga agcatctgac tgtcaccact    360
gccagtggct gtggaacagt cctgggccct gggccttggc tgctgtcaac agatgggctg    420
ggctgggctg tggtggggtg ggggacaacg ttggtaactc tgagaattca gctttggagt    480
cccgggtgag ggttttaga taaacccatc aatatcaccc acattctgtg actctttgca    540
tcactcgtgt tatttattta tttatttata ttctgccttg ttccagaaaa gtgtttaagg    600
caacaacgct tgttttttgg tgttttcttt tgacatttga aaatttagta cattgttaaa    660
atgtacttgt taaacaggta attttaaaga gaaggaacaa ttgtttttag taagttttct    720
ttttcctttt tcaatgaatt gattcttcaa attaaaagtt cttgagagaa ggagaggaag    780
atacagcaga cataggactg agccaaggaa gagtctgcct gagagagacg cttggcctgt    840
gctttgctgc catccgtgcg gccttggcca catccctatt aacagaggca gctccacttc    900
agacagggac aaggcttcct gctgtgcctt tctggcaggg ttttgtgggg tcacatggga    960
agcaatgtgt tacgcaagca gtctccatgt gtgtgtaaac tgctgtcctg gtgacttgtc   1020
cctcttctta gtggaaatgc atttgagatg gtgacagggc tggatgaacg tgtgaccctg   1080
ggagatccgg gctggactgt ggaccccgat gggccagagt ccttgtggcc cacagcatag   1140
cactggggac agagcgctct atgcaggtga ggcgtatgag aacagcatgg taaataattg   1200
atgaagtcac atttgttcaa cttaaaggat tgttctttat tctgaagtta ttttcttcct   1260
tatttggatg ataaaatttc cttttatgta atgaaggtaa aagtagaggg caatattttt   1320
gctttttgaa atgctcttgg ttgcaaaaca aaatgttggt tgctgtttgt cagccccaga   1380
atttcttctt aagttcgcct gtctctgaaa tcccaaagtc acggaaccgc agtctagctg   1440
tggtgcatgt ttacgtattg gtgagaaatt cctcttgggt tcttgaacag cctgtacgct   1500
ggcaggcagc actgcagcat ttctgctgct catggccaag aacgagtctg gagatcgctg   1560
cgtgcggttt taggaagtgc caacacccgt ggtgatgggc ctctggccac ccctgggatc   1620
catgggacac actcacagga agctgatgtg gccttctcgg tgaggactgc accttaacct   1680
gggcactggg agcctgtggc ccccctgtat gttggtgatg acactagtgt gggtcttctg   1740
gctctggggc tacagcttct gcctcctcac ctggccgtcg gtactcggca agcaggcctg   1800
gcctcccggg gcctggatcc ctaccggctg ggattggcct cctggaagta cctgtttggg   1860
ccatgtgacc tcctttctca cttatgcctc actcccctcc tcccgctcca aacccgaacc   1920
tctcagtgtg gaatgaacgc tccaaacccg aacctctcag tgtggaatga acgctccaaa   1980
cccgaacctc tcagtgtgga atgaaacagt ttagatgtgt acatgatgca cgtgggtggg   2040
attcacatcc caggagaatt ccacggagag gaatgtgcag attttgaagt gtacagtgat   2100
gtgtggaata aatactagaa attctcagca gacagtggga tggagaagtg agtgggggca   2160
```

-continued

```
ggagggggat ttctgttgcc ttgacatgtc gttgctcagt gcctggattg caggcgagtc   2220

tctctttttt atgttgcttt gatttcaaga tctcttagat atactaggta gtgtatgaat   2280

gtgcataaat ccagtttgag aatggtgttt atgaagaagc tgtttcgtgt gtacagttgc   2340

tgctgtaatt tagccagcag tgccctgccc tgccctgcag tgtctgctca gctcccactg   2400

cttctctttg ctgttgggca tgtgaggcat gacttggagg ggggcctggt gcctggggac   2460

ctgctgaaga gaatgctcac caccagctct ctgtttccct ttctgctttg gtaatcaaca   2520

cgtgtttgcc tgcagtggcc gggaccgtga ctgtttctgc ccttgtgcct agttaagagc   2580

cttcaaaagc ataatgaaca cttttgatat gatattgtaa ctttagtaaa tgctttactt   2640

ccctctaatt gcccccaaat gccttaattt tgtggactgt ttatttcaac aggtggaagt   2700

gttggtcgtg cgaaatcttg gtattcgcat ttcaagaagg gagttctttt ttctttcttc   2760

tttctatgga acgtttcaag tgattggata gaaagaaggg ctctgaagca ggagttttca   2820

cctgctctga gggaacttgg ggctccaggg acgtaccccc aaatgttgcc caggttgaaa   2880

ctccctgaca gcctgttcta cgtagtggct cgtggtttcc agtttgaaga gagttgtgcc   2940

cctaaaagtg tttgaaacct gtggctttca agcaaggtac cgttgtcccc acagtgttcc   3000

gtggggtagg gggtgatgga gactgtgggc aagcctgttg tttttggccc cctgttgtta   3060

catgggacct gttttgacgg tgggagggtg agatgtgaag atgtgggatg aacctggaat   3120

gaacgaatta aataaagaca tgcatccatc tgtcagcgaa aaagaaaaaa aaaa         3174


<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 20

gggacagatt gaggaggaag tg                                               22


<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 21

gcttgggtgt ctgtgttggt t                                                21


<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 22

actcctgaac acaccctgaa ga                                               22


<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 23
```

atctccatct gcctcatcaa c 21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 24
caccaacaga gcaggcaaat gt 22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 25
tgagccgtgg gatgtcataa ga 22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 26
ggaacaccag gtcgtatcaa ag 22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 27
gtgcgtcctt gatgaccact at 22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 28
gacccatccc aattcttaaa gc 22

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 29
agggatttcg gacggtctt 19

<210> SEQ ID NO 30
<211> LENGTH: 22
<212> TYPE: DNA

-continued

<213> ORGANISM: Artificial Sequence
<220> FEATURE:
<223> OTHER INFORMATION: Description of Artificial Sequence: Synthetic

<400> SEQUENCE: 30
ccaggagaag gagcagatca ag 22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 31
cggttggcaa tatcctcgta ct 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 32
acgctgaagt ccctgttttg tt 22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 33
ttcggctggc atttgactaa g 21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 34
gctcctatgc gggtgacaac 20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 35
gtcacacata ctccttggaa ga 22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 36
acagccacag atgaggatga t 21

-continued

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 37

cactggagat gacgctgatg                                                20


<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 38

gcccttgtgc ctagttaaga gc                                             22


<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 39

aggggcacaa ctctcttcaa ac                                             22
```